United States Patent [19]

Brooks et al.

[11] Patent Number: 4,992,464

[45] Date of Patent: Feb. 12, 1991

[54] HETEROARYL N-HYDROXY AMIDES AND UREAS WITH POLAR SUBSTITUENTS AS 5-LIPOXYGENASE INHIBITORS

[75] Inventors: Dee W. Brooks; James B. Summers, both of Libertyville, Ill.; Robert G. Maki, Kenosha, Wis.; Joseph F. Dellaria, Lindenhurst; Jimmie L. Moore, Gurnee, both of Ill.

[73] Assignee: Abbott Laboratories, Abbott Park, Ill.

[21] Appl. No.: 430,710

[22] Filed: Nov. 1, 1989

Related U.S. Application Data

[63] Continuation-in-part of Ser. No. 138,073, Jan. 19, 1988, Pat. No. 4,873,259, which is a continuation-in-part of Ser. No. 60,784, Jun. 19, 1987, abandoned, which is a continuation-in-part of Ser. No. 12,970, Feb. 19, 1987, abandoned.

[51] Int. Cl.$^5$ .................... A61K 31/38; C07D 333/56
[52] U.S. Cl. ........................ 514/443; 549/58
[58] Field of Search ................ 514/443; 549/58

[56] References Cited

U.S. PATENT DOCUMENTS 4,873,259  10/1989  Summers et al. .................. 514/443

Primary Examiner—Alan Siegel
Attorney, Agent, or Firm—Jerry F. Janssen; Andreas M. Danckers

[57] ABSTRACT

Compounds, compositions a method of inhibiting lipoxygenase and treating related disorders are disclosed. The compounds are of the formula:

Ar-A($R_2$)$_n$-N(OM)-CZ-$R_1$ wherein
Ar is

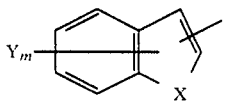

where
X is O, S, $SO_2$ or $NR_3$;
$R_3$ is hydrogen, alkyl, alkylaryl, alkoyl, alkylakoyl, aroyl or alkylaroyl;
Y is hydrogen, halogen, alkyl, alkenyl, cycloalkyl, aryl, arylalkyl, arylalkenyl, —OR, —SR, —COOR, —COR, —CON(R)$_2$, —OCOR, —N(R)$_2$, —O(CH)$_2$, —$SO_2$R, —$SO_2$N(R)$_2$, —O(CH$_2$)$_p$OR, —CN, —NO$_2$, —O(CH)$_p$O(CH$_2$)$_p$OR or —CF$_3$;
R is hydrogen, hydroxyl, alkyl, alkylaryl or aryl;
m is 0 to 5;
p is 1 to 4;
A is $C_1$–$C_{12}$ alkylene or $C_2$–$C_{14}$ alkenylene;
$R_2$ is —OR, —SR, —COOR, —COR, —CON(R)$_2$, —OCOR, —N(R)$_2$, —O(CH$_2$)$_y$CON(R)$_2$, —O(CH$_2$)$^y$OR, —CN, —NO$_2$, 1-tetrazolo, $C_4$–$C_8$ cyclic amido, imidazolo, —O(CH$_2$)$_y$O(CH$_2$)$_y$OR, —CF$_3$, —N(R) COCHR—NH(R), CONHCH(R)CO$_2$R, —OCOCHR-NH(R), —CR(NHR)CONR, —CR(NHR)COR, morpholino, —NH(CH$_2$)$_y$OH, —N[(CH$_2$)$_y$OH]$_2$, —N$_3$, —$SO_2$N(R)$_2$, —N(R)COR, —N(R)COOR, —N(R)CON(R)$_2$, —C(=NOH)NHOH or —C(=NOH)NH$_2$ where R is as defined above, y is 1 to 4 and —N(R)$_2$ can form a heterocyclic ring of 5–8 atoms;
M is hydrogen, a pharmaceutically acceptable cation or a metabolically cleavable group;
Z is oxygen or sulfur; and
$R_1$ us hydrogen, alkyl, alkenyl, —NR$_4$R$_5$, —NCOR$_6$ or —Q—(R$_2$)$_2$ where R$_4$ and R$_5$ independently selected from the group consisting of hydrogen, hydroxyl, alkyl, substituted alkyl with 1-3 substituents selected from the group consisting of $R_2$ as defined above, acyl, aryl and CON(R)$_2$ is as defined above, $R_6$ is hydrogen alkyl, alkylaryl, aryl or NR$_4$R$_5$ where R$_4$ and R$_5$ are as defined above and where NR$_4$R$_5$ can form a heterocyclic ring of a 5–8 atoms, Q is alkyl, alkenyl or aryl and z is 0 to 3; provided when n is O, $R_1$ is not hydrogen, alkyl, alkenyl, or NR$_4$R$_5$ wherein R$_4$ and R$_5$ are as defined above; and the pharmaceutically acceptable salts thereof.

3 Claims, No Drawings

HETEROARYL N-HYDROXY AMIDES AND UREAS WITH POLAR SUBSTITUENTS AS 5-LIPOXYGENASE INHIBITORS

TECHNICAL FIELD

This application is a continuation-in-part of U.S. application Ser. No. 138,073, filed Jan. 11, 1988, now U.S. Pat. No. 4,873,259 which is a continuation-in-part of U.S. application Ser. No. 060,784, filed June 10, 1987, now abandoned which is a continuation-in-part of U.S. application Ser. No. 012,970, filed Feb. 10, 1987 now abandoned. This invention relates to organic compounds which inhibit lipoxygenase enzymes. It also relates to methods and compositions involving inhibiting lipoxygenase enzymes in human and animal hosts in need of such treatment.

BACKGROUND OF THE INVENTION

The lipoxygenases are a family of enzymes which catalyze the oxygenation of arachidonic acid. The enzyme 5-lipoxygenase converts arachidonic acid to 5-hydroperoxy-eicosatetraenoic acid (5-HPETE). This is the first step in the metabolic pathway yielding 5-hydroxyeicosatetraenoic acid (5-HETE) and the important class of potent biological mediators, the leukotrienes (LTs). Similarly 12- and 15-lipoxygenase convert arachidonic acid to 12- and 15-HPETE respectively. Biochemical reduction of 12-HPETE leads to 12-HETE, while 15-HPETE is the precursor of the class of biological agents known as the lipoxins. 12-HETE has been found in high levels in epidermal tissue of patients with psoriasis. Lipoxins have recently been shown to stimulate elastase and superoxide ion release from neutrophils.

A variety of biological effects are associated with these products from lipoxygenase metabolism of arachidonic acid and they have been implicated as mediators in various disease states. For example, the LTs $C_4$ and $D_4$ are potent constrictors of human airways in vitro and aerosol administration of these substances to non-asthmatic volunteers induces bronchoconstriction. $LTB_4$ and 5-HETE are potent chemotactic factors for inflammatory cells such as polymorphonuclear leukocytes. They also have been found in the synovial fluid of rheumatoid arthritic patients. Leukotrienes have been implicated as important mediators in allergic rhinitis, psoriasis, adult respiratory distress syndrome, inflammatory bowel disease, endotoxin shock, and ischemia induced myocardial injury. The biological activity of the LTs has been reviewed by Lewis and Austen, *J. Clinical Invest.* 73, 89, 1984 and by J. Sirois, *Adv. Lipid Res.*, 21, 78, (1985).

Thus, lipoxygenase enzymes are believed to play an important role in the biosynthesis of mediators of asthma, allergy, arthritis, psoriasis, and inflammation. Agents which block or modulate the activity of lipoxygenase enzymes will likely be useful in the treatment of diseases involving leukotriene pathogenesis. Some examples of 5-lipoxygenase inhibitors known to the art are: AA-861, disclosed in U.S. Pat. No. 4,393,075, issued July 12, 1983, to Terro et al., pyrazolopyridines, disclosed in European Patent Application of Iriburn et al., S. N. 121,806, published Oct. 17, 1984; arachidonyl hydroxamic acid, disclosed in E. J. Corey et al., *J. Am. Chem. Soc.*, 106, 1503 (1984) and European Patent Application of P. H. Nelson, Ser. No. 104,468, published Apr. 4, 1984; BW-755C, disclosed in Radmark et al., *FEBS Lett.* 110, 213,(1980); nordihydroguaiaretic acid, disclosed in Marris et al., *Prostaolandins,* 19, 371 (1980); Rev-5901, disclosed in Coutts, Meeting Abstract 70, *Prostaglandins and Leukotrienes* '84; benzoxaprofen, disclosed in J. Walker, *Pharm. Pharmacol.*, 31, 778 (1979), and hydroxamic acids, disclosed in U.S. Pat. Nos. 4,608,390 and 4,623,661, issued Aug. 16, and Nov. 18, 1986 respectively.

SUMMARY OF THE INVENTION

The compounds of this invention possess unexpected activity as inhibitors of lipoxygenase enzymes, and reduce the biosynthesis of leukotrienes $B_4$, $C_4$, $D_4$ and $E_4$. The compounds and compositions containing these compounds are useful for the treatment of disease states, in mammals, which involve leukotrienes $B_4$, $C_4$, $D_4$ and $E_4$.

The compounds of this invention are those of Formula I:

$$Ar\text{—}A(R_2)_n\text{—}N(OM)\text{—}CZ\text{—}R_1$$

wherein
Ar is

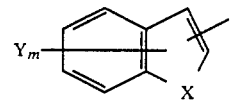

where
X is O, S, $SO_2$ or $NR_3$;
$R_3$ is hydrogen, alkyl, alkylaryl, alkoyl, alkylalkoyl, aroyl or alkylaroyl;
Y is hydrogen, halogen, alkyl, alkenyl, cycloalkyl, aryl, arylalkyl, arylalkenyl, —OR, —SR, —COOR, —COR, —CON(R)$_2$, —OCOR, —N(R)$_2$, —O(CH$_2$)$_p$ CON(R)$_2$, —SO$_2$R, —SO$_2$N(R)$_2$, —O(CH$_2$)$_p$OR, —CN, —NO$_2$, —O(CH$_2$)$_p$O(CH$_2$)$_p$OR or —CF$_3$;
R is hydrogen, hydroxyl, alkyl, alkylaryl or aryl;
m is 0 to 5;
p is 1 to 4;
A is $C_1$-$C_{12}$ alkylene or $C_2$-$C_{14}$ alkenylene;
$R_2$ is —OR, —SR, —COOR, —COR, —CON(R)$_2$, —OCOR, —N(R)$_2$, —O(CH$_2$)$_y$CON(R)$_2$, —O(CH$_2$)$_y$OR, —CN, —NO$_2$, 1-tetrazolo, $C_4$-$C_8$ cyclic amido, imidazolo, —O(CH$_2$)$_y$O(CH$_2$)$_y$OR, —CF$_3$, —N(R)CO-CHR—NH(R), —CONHCH(R)CO$_2$R, —OCO-CHR—NH(R), —CR(NHR)CONR, —CR(NHR)COR, morpholino, —NH(CH$_2$)$_y$OH, —N[(CH$_2$)$_y$OH]$_2$, —N$_3$, —SO$_2$R, —SO$_2$N(R)$_2$, —N(R)COR, —N(R)COOR, —N(R)CON(R)$_2$, —C(=NOH)NHOH or —C(=NOH)NH$_z$ where R is as defined above, y is 1 to 4 and —N(R)$_2$ can form a heterocyclic ring of 5-8 atoms;
M is hydrogen, a pharmaceutically acceptable cation or a metabolically cleavable group;
Z is oxygen or sulfur; and
$R_1$ is hydrogen, alkyl, alkenyl, —NR$_4$R$_5$, —N-COR$_6$ or —Q—(P$_2$)$_z$ where R$_4$ and R$_5$ are independently selected from the group consisting of hydrogen, hydroxyl, alkyl, substituted alkyl with 1-3 substituents selected from the group consisting of R$_2$ as defined above, acyl, aryl and CON(R)$_2$ were R$_2$ is as defined above, R$_6$ is hydrogen, alkyl, alkylaryl, aryl or $NR_4R_5$ where $R_4$ and $R_5$ are as defined above and where $NR_4R_5$ can form a heterocyclic ring of 5-8 atoms, Q is alkyl, alkenyl or aryl and z is 0 to 3; provided when n is O, $R_1$ is not hydrogen, alkyl, alkenyl, or $NR_4R_5$ wherein $R_4$ and $R_5$ are as defined above; and the pharmaceutically acceptable salts thereof.

This invention also relates to pharmaceutical compositions and methods of inhibiting lipoxygenase enzymes and related disorders comprising the administration of a compound of Formula I to a mammal, preferably a human, in need of such treatment.

DETAILED DESCRIPTION OF THE INVENTION

The present invention provides for compounds which exhibit unexpected activity for lipoxygenase enzyme inhibition, particularly, 5-lipoxygenase, and thereby reduce the biosynthesis of leukotrienes $B_4$, $C_4$, $D_4$, and $E_4$.

The compounds of this invention are those of Formula I:

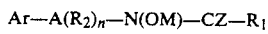

wherein
Ar is

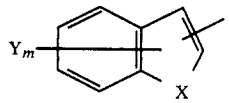

where
X is O, S, $SO_2$ or $NR_3$;
$R_3$ is hydrogen, alkyl, alkylaryl, alkoyl, alkylalkoyl, aroyl or alkylaroyl;
Y is hydrogen, halogen, alkyl, alkenyl, cycloalkyl, aryl, arylalkyl, arylalkenyl, —OR, —SR, —COOR, —COR, —CON(R)$_2$, —OCOR, —N(R)$_2$, —O(CH$_2$)$_p$CON(R)$_2$, —SO$_2$R, —SO$_2$N(R)$_2$, —O(CH$_2$)$_p$OR, —CN, —NO$_2$, —O(CH$_2$)$_p$O(CH$_2$)$_p$OR or —CF$_3$;
R is hydrogen, hydroxyl, alkyl, alkylaryl or aryl;
m is 0 to 5;
p is 1 to 4;
A is $C_1$-$C_{12}$ alkylene or $C_2$-$C_{14}$ alkenylene;
$R_2$ is —OR, —SR, —COOR, —COR, —CON(R)$_2$, —OCOR, —N(R)$_2$, —O(CH$_2$)$_y$CON(R)$_2$, —O(CH$_2$)$_y$OR, —CN, —NO$_2$, 1-tetrazolo, $C_4$-$C_8$ cyclic amido, imidazolo, —O(CH$_2$)$_y$O(CH$_2$)$_y$OR, —CF$_3$, —N(R)COCHR—NH(R), —CONHCH(R)CO$_2$R, —OCOCHR—NH(R), —CR(NHR)CONR, —CR(NHR)COR, morpholino, —NH(CH$_2$)$_y$OH, —N[(CH$_2$)$_y$OH]$_2$, —N$_3$, —SO$_2$R, —SO$_2$N(R)$_2$, —N(R)COR, —N(R)COOR, —N(R)CON(R)$_2$, —C(=NOH)NHOH or —C(=NOH)NH$_z$ where R is as defined above, y is 1 to 4 and —N(R)$_2$ can form a heterocyclic ring of 5-8 atoms;
M is hydrogen, a pharmaceutically acceptable cation or a metabolically cleavable group;
Z is oxygen or sulfur; and
$R_1$ is hydrogen, alkyl, alkenyl, —NR$_4$R$_5$, —NCOR$_6$ or —Q—(R$_2$)$_z$ where $R_4$ and $R_5$ are independently selected from the group consisting of hydrogen, hydroxyl, alkyl, substituted alkyl with 1-3 substituents selected from the group consisting of $R_2$ as defined above, acyl, aryl and CON(R)$_2$ were $R_2$ is as defined above, $R_6$ is hydrogen, alkyl, alkylaryl, aryl or $NR_4R_5$ where $R_4$ and $R_5$ are as defined above and where $NR_4R_5$ can form a heterocyclic ring of 5-8 atoms, Q is alkyl, alkenyl or aryl and z is 0 to 3; provided when n is O, $R_1$ is not hydrogen, alkyl, alkenyl, or $NR_4R_5$ wherein $R_4$ and $R_5$ are as defined above; and the pharmaceutically acceptable salts thereof.

This invention also relates to pharmaceutical compositions and methods of inhibiting lipoxygenase enzymes and related disorders comprising the administration of a compound of Formula I to a mammal, preferably a human, in need of such treatment.

$R_4$, $R_5$ and $R_6$ each may be independently substituted with any substituent as herein defined for $R_2$.

The term "alkyl" as used herein refers to straight and branched chain radicals having 1 to 12 carbon atoms which may be optionally substituted as herein defined above. Representative of such radicals are methyl, ethyl, n-propyl, isopropyl, n-butyl, secbutyl, isobutyl, tert-butyl, and the like.

The term "alkenyl" as used herein refers to straight and branched chain unsaturated radicals having 2 to 12 carbon atoms, which may be optionally substituted as defined above. Representative of such groups are ethenyl, 1-propenyl, 2-propenyl, 2-methyl-1-propenyl, 1-butenyl, 2-butenyl, and the like.

The term "alkylene" as used herein refers to straight and branched chain linking groups having 1 to 6 carbon atoms. Representative of such groups are methylene, ethylene, trimethylene, tetramethylene, 2-methyltrimethylene and 2,2-dimethyltrimethylene.

The term "alkenylene" as used herein refers to straight or branched chain linking groups having 2 to 6 carbon atoms. Representative of such groups are ethenylene and propenylene.

The term "aryl" as used herein refers to mono or polycyclic hydrocarbon group containing fused or non-fused aromatic ring systems which may contain one or more hetero atoms such as O, N or S in the ring system and which may be optionally substituted as defined herein. Representative of such groups are phenyl, naphthyl, biphenyl, triphenyl, pyridinyl, pyrrolyl, pyrimidinyl, furyl, thienyl, indolyl, pyrazinyl, isoquinolyl, benzopyranyl, benzofuryl, benzothiophinyl, imidazolyl, carbazolyl, and the like.

The term "aroyl" as used herein refers to the radical aryl-CO- wherein the aryl ring may be optionally substituted as herein before defined.

The term "alkoxy" as used herein refers to straight and branched chain oxygen ether radicals having 1 to 12 carbon atoms which may be optionally substituted. Representative of such groups are methoxy, ethoxy, isopropoxy, n-butoxy, sec-butoxy, isobutoxy, tert-butoxy, and the like.

The term "aryloxy" as used herein refers to substituted or unsubstituted aryl ethers which may be optionally substituted as herein before defined. Representative of such groups are 4-acetylphenoxy, phenoxy, 1-naphthoxy, 2-naphthoxy, and the like.

The terms "cycloalkyl" and "cycloalkenyl" as used herein refer to saturated and unsaturated cyclic or bicyclic radicals having 3 to 12 carbon atoms which may be optionally substituted as defined above. Representative of such groups are cyclopropyl, cyclobutyl, cyclopentyl, cyclohexyl, norbornyl, 2-chlorocyclohexyl, and the like.

The term "cyclic amide" as used herein refers to cyclic radicals containing 4 to 8 carbon atoms and an amido linkage.

The terms "halo" and "halogen" as used herein refer to radicals derived from the elements fluorine, chlorine, bromine and iodine.

The term "halo-substituted" alkyl and alkenyl refers to a radical as described above substituted with one or more halogens, and which may also be additionally substituted as defined above. Representatives of such groups are chloromethyl, trifluoromethyl, 2,2,2-trichloroethyl, 2,2-dichloro-1-hydroxybutyl, and the like.

The term "thioalkyl" as used herein refers to —$SR_9$ wherein $R_9$ is an alkyl radical, including, but not limited to thiomethyl, thioethyl, thioisopropyl, n-thiobutyl, sec-thiobutyl, isothiobutyl, tert-thiobutyl, and the like.

The term "alkoyl" as used herein refers to —$COR_{10}$ wherein $R_{10}$ is an alkyl radical, including, but not limited to formyl, acetyl, propionyl, butyryl, isobutyryl, pivaloyl, and the like.

The term "carboalkoxy" as used herein refers to —$COR_{11}$ wherein $R_{11}$ is an alkoxy radical, including, but not limited to carbomethoxy, carboethoxy, carboisopropoxy, carbobutoxy, carbosec-butoxy, carboisobutoxy, carbotert-butoxy, and the like.

The term "arylalkoxy" as used herein refers to —$OR_{14}$ wherein $R_{14}$ is an arylalkyl radical, including, but not limited to phenylmethoxy (i.e., benzyloxy), 4-fluorobenzyloxy, 1-phenylethoxy, 2-phenylethoxy, diphenylmethoxy, 1-naphthylmethoxy, 2-naphtylmethoxy, 9-fluorenoxy, 2-, 3- or 4-pyridylmethoxy, 2-, 3-, 4-, 5-, 6-, 7-, 8-quinolylmethoxy, and the like.

The term "arylthioalkoxy" as used herein refers to —$SR_{15}$ wherein $R_{15}$ is an arylalkyl radical, including, but not limited to phenylthiomethoxy (i.e., thiobenzyloxy), 4-fluorothiobenzyloxy, 1-phenylthioethyoxy, 2-phenylthioethoxy, diphenylthiomethoxy, 1-naphthylthiomethoxy, and the like.

The term "arylalkyl" as used herein refers to an aryl group appended to an alkyl radical, including, but not limited to phenylmethyl (benzyl), 1-phenylethyl, 2-phenylethyl, 1-naphthylethyl, 2-pyridylmethyl, and the like.

The term "arylalkenyl" as used herein refers to an aryl group appended to an alkenyl radical, including, but not limited to phenylethenyl, 3-phenylprop-1-enyl, 3-phenylprop-2-enyl, 1-naphthylethenyl, and the like.

The term "alkylsulfonyl" as used herein refers to —$SO_2R_{16}$ wherein $R_{16}$ is an alkyl radical, including, but not limited to methylsulfonyl (i.e., mesityl), ethyl sulfonyl, isopropylsulfonyl, and the like.

All of the alkyl, alkenyl, alkylene, alkenylene, aryloxy, cycloalkyl, cycloalkenyl, aryl and arylalkyl radicals may in turn be substituted with various groups as defined above. Representative of this group are 2-chlorophenyl-1-naphthyl, 2,4-dichloro-phenyl-4-benzyl and 2-fluoromethyl- cyclohexyl-methyl.

The term "pharmaceutically acceptable cation" as used herein means a non-toxic cation based on the alkali and alkaline earth metals, such as sodium, lithium, potassium, calcium, magnesium and the like, as well as those based on non-toxic ammonium, quaternary ammonium and amine cations, including, but not limited to, ammonium, tetramethylammonium, tetraethylammonium, methylamino, dimethylamino, trimethylamino, triethylamino and ethylamino cations.

The term "metabolically cleavable group" as used herein refers to groups which can be cleaved from the molecule by metabolic processes and can be substituted with a hydrogen, a salt, or form a group which yields an active enzyme inhibitor when the cleavable group is removed from the molecule. Examples of metabolically cleavable groups include COR, COOR, CONRR and $CH_2OR$ radicals where R is selected independently at each occurrence from alkyl, aryl or an aryl substituted with one or more alkyl, halogen, hydroxy or alkoxy groups. Representative metabolically cleavable groups include acetyl, methoxycarbonyl, benzoyl, tetrahydropyranyl, methoxymethyl and trimethylsilyl groups.

The term "pharmaceutically acceptable salts" refers to the relatively non-toxic, inorganic or organic acid addition salts and alkaline earth metal salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, lauryl sulphate, and the like. Representative alkali or alkaline earth metal sales include sodium, calcium, potassium and magnesium salts, and the like. It will be apparent to those skilled in the art that, depending upon the number of available amino groups for salt formation, the salts of this invention can be per-N-salts.

Certain compounds of this invention may exist in optically active forms. The R and S isomers and mixtures thereof, including racemic mixtures as well as the cis and trans mixtures are contemplated by this invention. Additional asymmetric carbon atoms may be present in a substituent group such as an alkyl group. All such isomers as well as the mixtures thereof are intended to be included in the invention.

The present invention includes one or more of the compounds of Formula I formulated into compositions together with one or more non-toxic pharmaceutically acceptable carriers, adjuvants or vehicles which are collectively referred to herein as carriers, for parenteral injection, for oral administration in solid or liquid form, for rectal administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills and granules can be prepared with coatings and shells, such as enteric coatings and others well known in this art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration include powders, sprays and inhalants. The active ingredient is admixed under sterile conditions with a pharmaceutically acceptable carrier and any needed preservatives, buffers or propellants as may be required. Ophthalmic formulations, eye ointments, powders and solutions are also contemplated as being within the scope of this invention.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds of this invention administered to a host in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Several synthetic methods may be used to prepare compounds of this invention. Some of these methods are described in copending U.S. patent application Ser. No. 138,073, filed Jan. 11, 1988, incorporated herein by reference.

The compounds of Examples 1-79 may also be prepared by the following general procedure as set forth in Procedure A, Procedure B and Procedure C.

Procedure A—Oxime Formation

A 0.2 M solution of the ketone in 1:1 pyridine:ethanol containing 1.1 equivalents of hydroxylamine hydrochloride is stirred at room temperature until thin layer chromatography reveals that all starting material is consumed (4-18 hours). The reaction is then concentrated in vacuo. The residue is taken up in water and extracted with ethyl acetate (3x). The combined organic extract is dried with MgSO4 and concentrated to afford the corresponding oxime.

Procedure B—Oxime Reduction to Hydroxylamine

To a 0.2 M solution of the oxime in ethanol, is added 2.1 equivalents of BH3.pyridine. After 30 minutes, 2.4 equivalents of 6N HCl is added and the reaction is stirred for 18 hours. The mixture is neutralized with 2N NaOH, diluted with brine, and extracted with ethyl acetate (3x). The combined organic extract is dried with MgSO4 and concentrated. The resulting residue is purified by chromatography on silica gel to yield the desired hydroxylamine.

Procedure C—N-Hydroxy Urea Preparation

To a 0.2 M solution of the hydroxylamine in THF, is added 1.2 equivalents of trimethylsilylisocyanate. After stirring for 15 minutes, the reaction was diluted with aqueous saturated NH4Cl and extracted with EtOAc (3x). The combined organic extract is dried with MgSO4 and concentrated to afford the desired N-hydroxy urea.

The following examples illustrate the preparation and use of the compounds of this invention.

EXAMPLE 1

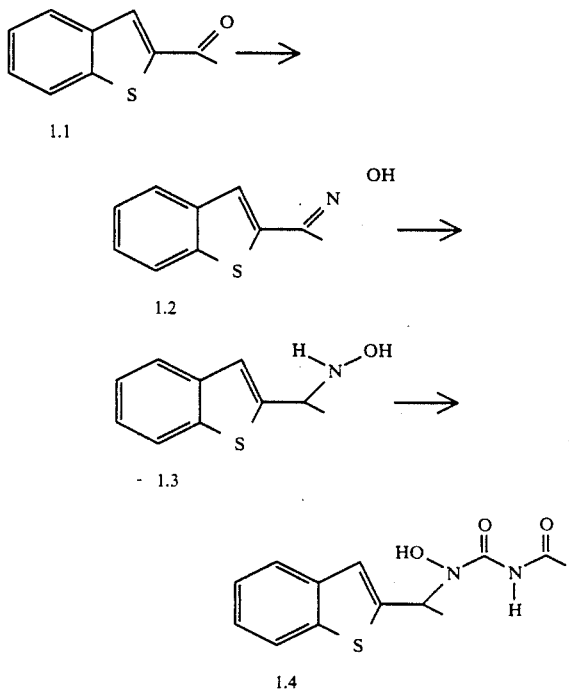

(a) To a solution of 2-acetylbenzothiophene (9.15 g, 52 mmol) in a mixture of ethanol:pyridine(1:1, 250 mL) was added hydroxylamine hydrochloride (3.6g, 52 mmol). This mixture was heated for 1 hour at 90° C., then cooled to room temperature. The solution was concentrated in vacuo. The crude residue was taken up in EtOAc and washed with water. The aqueous wash was back-extracted twice with EtOAc. The combined organic extract was dried with MgSO4 and concentrated. The resulting solid was crystallized twice from 95% ethanol to afford the corresponding oxime.

(b) To a solution of the oxime prepared in step (a) (8.89 g, 46.5 mmol) in ethanol (200 mL), was added BH3.pyridine (9.08 g, 97.7 mmol). After stirring for 2.5 hours, 6N HCl (20.15 mL, 2.6 mmol) was added and the reaction was stirred for 3.5 hours. The mixture was then neutralized with 2N NaOH and diluted further with brine (150 mL). The resulting aqueous solution was extracted with ethyl acetate (3×200 mL). The combined organic extract was dried with MgSO4 and concentrated to provide a crude residue which was chromatographed (silica gel, ether:hexanes, 1:4) and afforded the corresponding hydroxylamine.

(c) To a solution of the hydroxylamine prepared in step (b) (1.50 g, 7.8 mmol) in tetrahydrofuran (THF, 25 mL) was added (37.0 mL, 9.3 mmol) of a 0.25M ether solution of acylisocyanate prepared by the method of R. C. Cambie, P. F. Davis, P. S. Rutledge, P. D. Woodgate, *Aust. J. Chem.* 1984, 34, 2073–84). The reaction was stirred for 15 minutes, then diluted with brine (25 mL). This aqueous solution was extracted with ethyl acetate (×25 mL). The combined organic extract was dried with MgSO4 and concentrated. Crystallization from ether-hexanes afforded the desired N-hydroxy urea, 1.43 g. m.p. 134.0–136.5.° C.; NMR (300 MHz, DMSO-d6) 1.59 (3H, d, J=7 Hz), 2.25 (3H, s), 5.69 (1H, q, J=7Hz), 7.34 (3H, m), 7.80 (1H, m), 7.90 (1H, m), 9.36 (1H, bs), 9.98 (1H, bs); MS+ =279. Analysis Calc'd for $C_{13}H_{14}N_2O_3S$: C, 56.10; H, 5.07; N, 10.07. Abbott D-16,969 Found: C, 56.14; H, 5.18; N, 10.10.

EXAMPLE 2

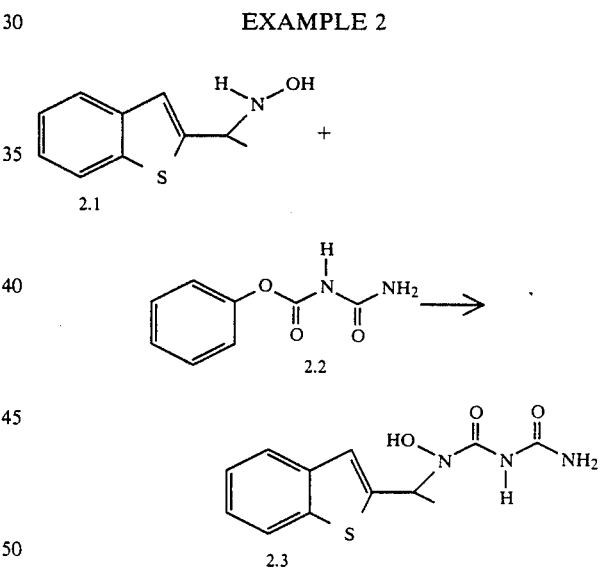

(a) Urea (7.27 g, 119.9 mmol) was added to phenyl chloroformate (8.94 g, 57.1 mmol) followed by pyridine (30 mL) and the resulting mixture became highly exothermic and soon solidified. This solid residue was dispersed and washed well with EtOAc and pyridine to afford the corresponding hydroxylamine (2.2) as a white solid.

(b) A solution of the hydroxylamine prepared in step (a) (0.5 g, 2.591 mmol) and 2.2 (0.47 g, 2.591 mmol) in dioxane (12 mL) was heated at 50° C. for 18 hours and 75° C. for 24 hours. The reaction was then cooled to room temperature and concentrated in vacuo. The resulting residue was crystallized from ethanol-hexanes to afford 2.3, 133 mg. m.p. 180° C. (dec); NMR(300 MHz DMSO-d6) 1.59 (3H d. J=7 Hz), 5.67 (1H, q, J=6Hz), 7.15 (1H, bs), 7.33 (3H, m), 7.65 (1H, bs), 7.80 (1H, m), 7.91 (1H, m), 8.49 (1H, bs), 10.01 (1H, bs); MS: M+ =280.

Analysis Calc'd for $C_{12}H_{13}N_3O_3S$: C, 52.73; H, 4.79; N, 15.37. Found: C, 50.89; H, 4.83; N, 14.98.

EXAMPLE 3

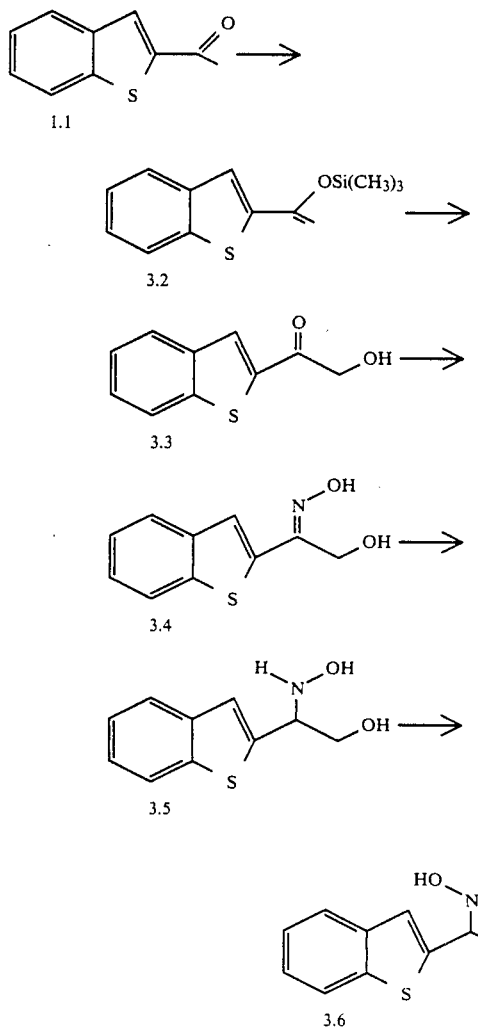

(a) To a solution of di-isopropylamine (0.63 g, 6.3 mmol) in THF (20 mL) at 0° C., was added dropwise n-BuLi (2.52 mL of 2.5M in hexanes, 6.3 mmol). This solution was stirred for 20 minutes, then cooled to −78° C. and 2-acetylbenzothiophene (1.00 g, 5.7 mmol) in THF (5 mL), was added dropwise and the resulting mixture was stirred at −78° C. for 20 minutes. Chlorotrimethylsilane (0.68 g, 6.3 mmol) was added and the reaction was stirred for 40 minutes. The reaction was diluted with aqueous saturated NaHCO$_3$ (25 mL), warmed to room temperature and extracted with EtOAc (3×25 mL). The combined organic extract was dried with MgSO$_4$ and concentrated to afford 3.2 as a crude oil.

(b) The intermediate prepared in step (a) was dissolved in CH$_2$Cl$_2$ (25 mL) and m-chloroperoxybenzoic acid (1.18 g, 6.84 mmol) was added. After stirring for 1 hour, the mixture was diluted with aqueous saturated NaHCO$_3$ (25 mL) and extracted with CH$_2$Cl$_2$ (3×25 mL). The combined organic extract was dried with MgSO$_4$ and concentrated to 25 mL. To this solution was added a few beads of Amberlyst-15 ion exchange resin and the mixture was stirred for 30 minutes, filtered and concentrated. The resulting residue was chromatographed (silica gel, ether-hexanes, 1:1) and afforded 740 mg of 3.3 as a white solid.

(c) The intermediate prepared in step (b) was converted by Procedure A to afford 3.4.

(d) The intermediate prepared in step (c) was converted by Procedure B to afford 338 mg of 3.5.

(e) The intermediate prepared in step (d) was converted by Procedure C to yield 162 mg of 3.6 m.p. 142–148° C. (dec); NMR (300 MHz, DMSO-d$_6$) 3.73–3.92 (2H, sm), 4.82 (1H, dd, J=6 Hz), 5.44 (1H, t, J=7 Hz), 6.42 (2H, bs), 7.31 (3H, m), 7.78 (1H, m), 7.88 (1H, m), 9.26 (1H, s); MS: M+ =253.

Analysis Calc'd for $C_{11}H_{12}N_2O_3S$: C, 52.36; H, 4.80; N, 11.11. Found: C, 52.13; H, 4.87; N, 10.88.

EXAMPLE 4

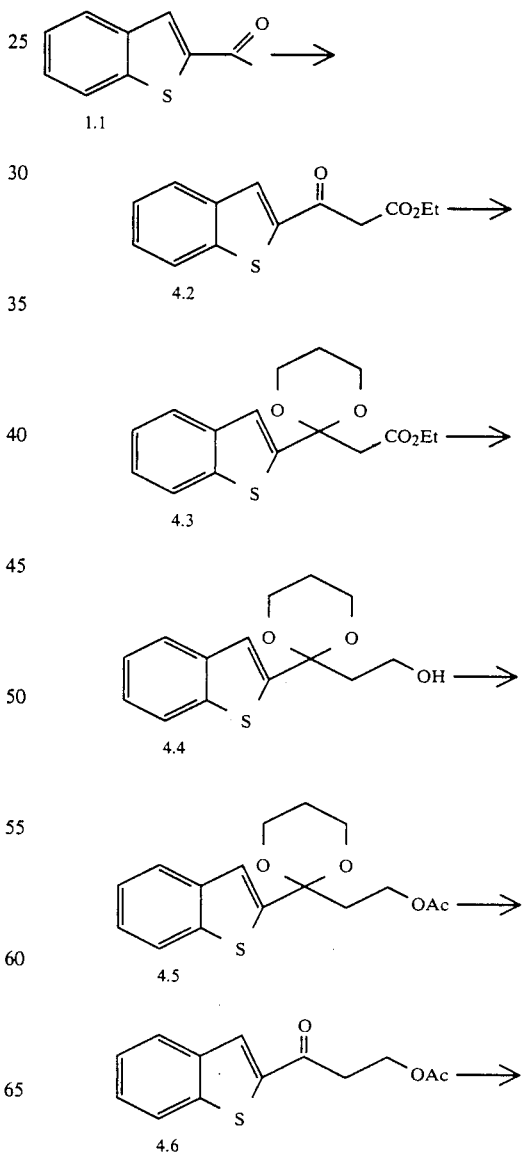

-continued

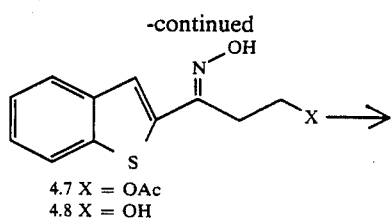

4.7 X = OAc
4.8 X = OH

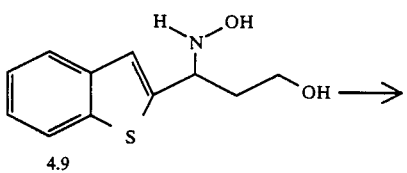

4.9

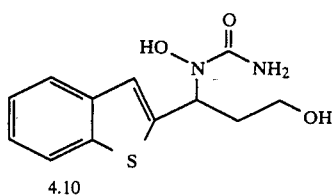

4.10

(a) To a stirred solution of 2-acetylbenzothiophene (5.00 g, 28.4 mmol) in diethyl carbonate (75 mL) at 0° C., was added slowly NaH (60% oil dispersion, 1.41 g, 58.8 mmol). The mixture was refluxed for 1.5 hours and the resulting gel was poured into ice water (200 mL) containing acetic acid (7.5 mL). This aqueous solution was then extracted with EtOAc (3×200 mL) and the combined organic extract was dried with MgSO4 and concentrated. The resulting residue was chromatographed (silica gel, ether-hexanes, 1:4) and afforded 6.60 g of 4.2.

(b) To a stirred solution of the product of step (a) (6.60 g, 26.6 mmol) in benzene (125 mL) was added ethylene glycol (14.8 mL, 266 mmol) along with a catalytic amount of p-toluene sulfonic acid. The reaction was then refluxed for 48 hours with removal of water via a Dean-Stark trap. The reaction was diluted with aqueous saturated NaHCO3 (125 mL), and extracted with EtOAc (3×125 mL). The combined organic extract was dried with MgSO4 and concentrated to afford 4.3.

(c) To a suspension of LAH (1.01 g, 26.6 mmol) in ether (125 mL) at 0° C. was added a solution of the product of step (b) in ether (20 mL). The reaction was allowed to warm to room temperature and was then refluxed for 4.5 hours. The reaction was cooled and then quenched slowly by the dropwise addition of aqueous saturated NH4Cl. The solution was dried with solid Na2SO4, then filtered through Celite and concentrated. The resulting residue was chromatographed (silica gel, ether-hexanes, 1:1) and afforded 4.69 g of 4.4.

(d) To a stirred solution of the product of step (c) (1.50 g, 6.0 mmol) in pyridine (30 mL) was added acetic anhydride (674 mg, 6.6 mmol). After stirring for 1 hour, the reaction was diluted with 1N HCl (30 mL), and extracted with EtOAc (3×30 mL). The combined organic extract was dried with MgSO4 and concentrated to afford 4.5.

(e) A solution of the intermediate prepared in step (d) in 1:1, 1N HCl:THF (30mL) was stirred for 18 hours. The mixture was then extracted with EtOAc (3'20 mL). The combined organic extract was dried with MgSO4 and concentrated. The resulting residue was chromatographed (silica gel, ether-hexanes, 1:4) and afforded 606 mg of 4.6.

(f) The intermediate prepared in step (e) was converted by Procedure A to afford 4.7.

(g) To a stirred solution of the product of step (f) (10.1 mmol) in methanol (40 mL), was added K2CO3 (1.40 g, 10.1 mmol). After stirring 1 hour, the reaction was diluted with pH7 buffer (50 mL) and extracted with EtOAc (3×50 mL). The combined organic extract was dried with MgSO4 and concentrated to afford 4.8.

(h) The intermediate prepared in step (g) was converted by Procedure B to afford 4.9.

(i) The intermediate prepared in step (h) was converted by Procedure C to afford 4.10. m.p. 144° C. (dec); NMR (300 MHz, DMSO-d6) 1.92–2.05 (1H, m), 2.07–2.20 (1H, m), 3.37–3.55 (2H, m), 4.52 (1H, t, J=5 Hz), 5.58 (1H, t, J=7.5 Hz), 6.38 (2H, bs), 7.30 (3H, m), 7.78 (1H, m), 7.88 (1H, m), 9.27 (1H, s); MS: M+=267.
Analysis Calc'd for C12H14N2O3S: C, 54.12; H, 5.30; N, 10.52.
Found: C, 53.89; H, 5.44; N, 10.22.

EXAMPLE 5

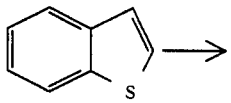

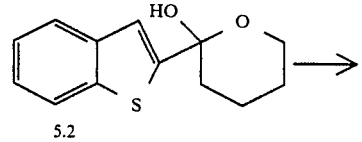

5.2

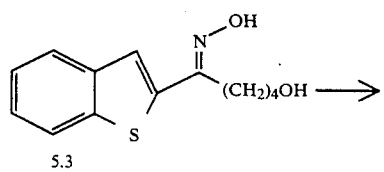

5.3

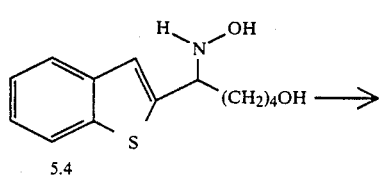

5.4

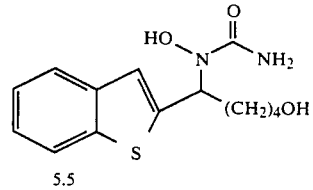

5.5

(a) To a stirred solution of thionaphthene (1.0 g, 7.5 mmol) in THF (40 mL) at −78° C., was added dropwise n-BuLi (3.00 mL of a 2.5 M solution, 7.5 mmol). After stirring for 30 minutes at −78° C., d-valerolactone (0.75 g, 7.5 mmol) was added and the mixture was stirred for 1.5 hours. The reaction was then diluted with aqueous saturated NH4Cl (40 mL), warmed to room temperature, and extracted with EtOAc (3×40 mL). The combined organic extract was dried with MgSO4 and concentrated. The resulting white solid was washed with ether to afford 1.60 g of 5.2.

(b) The intermediate prepared in step (a) was converted by Procedure A to afford 5.3.

(c) The intermediate prepared in step (b) was converted by Procedure B to afford 5.4.

(d) The intermediate prepared in step (c) was converted by Procedure C to afford 5.5 m.p. 165–166° C.; NMR (300 MHz, DMSO-$d_6$) 1.24–1.53 (4H, m), 1.60–2.03 (2H, m), 3.39 (2H t under DMSO) 4.37 (1H bt), 5.39 (1H, t, J=8.5 Hz), 6.37 (2H, bs), 7.30 (3H, m), 7.77 (1H, m), 7.88 (1H, m), 9.25 (1H, s); MS: M+ =295.

Analysis Calc'd for $C_{14}H_{18}N_2O_3S$: C, 57.12; H, 6.16; N, 9.52.

Found: C, 56.97; H, 6.30; N, 9.19.

EXAMPLE 6

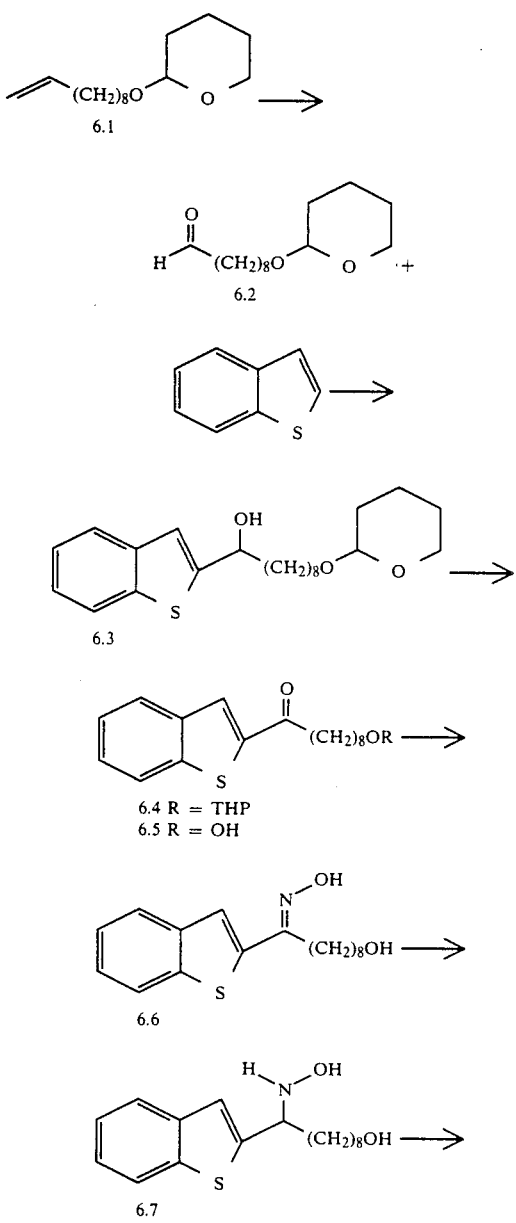

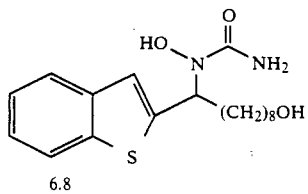

(a) To a stirred solution of 9-decenol (1.0g, 6.4 mmol) and 2,3-dihydropyran (0.81 g, 9.6 mmol) in $CH_2Cl_2$ (30 mL) was added Amberlyst-15 ion exchange resin (0.1 g) and the suspension was stirred for 3.5 hours. More dihydropyran (0.81 g, 9.6 mmol) was added and the reaction was stirred for 30 minutes, filtered and concentrated. The resulting residue was chromatographed (silica gel, ether-hexanes, 2.5:97.5) and afforded 1.25 g of 6.1 as a colorless oil.

(b) A mixture of ozone and oxygen gas was bubbled through a stirred mixture of the compound prepared in step (a) (4.55 g, 19 mmol) in 1:1 $CH_2Cl_2$:MeOH (100mL) containing $NaHCO_3$ (0.1 g) at −78° C. until a blue tint was apparent in the reaction mixture. Then nitrogen gas was then bubbled through the mixture to remove excess ozone. Dimethylsulfide (11.78 g, 190 mmol) was added, the cooling bath was withdrawn and the mixture was stirred for 18 hours at room temperature. The mixture was filtered and concentrated. The resulting residue was chromatographed (silica gel, ether-hexanes, 1.9) and afforded 4.18 g of 6.2 as a colorless oil.

(c) To a stirred solution of thionaphthene (0.46 g, 3.39 mmol) in THF (15 mL) at −78° C., was added dropwise n-BuLi (1.36 mL of 2.5 M, 3.39 mmol). The mixture was stirred for 30 minutes at −78° C. after which a solution of the product of step (b) (0.82 g, 3.39 mmol) in THF (2 mL) was added dropwise. After stirring for 20 minutes, the mixture was diluted with aqueous saturated $NH_4Cl$ (15 mL), allowed to warm to room temperature and extracted with ethyl acetate (3×15 mL). The combined organic extract was dried with $MgSO_4$ and concentrated. The resulting residue was chromatographed (silica gel, ether-hexanes, 1:3) and afforded 1.02 g of 6.3 as a colorless oil.

(d) To a solution of oxalyl chloride (2.25 g, 17.7 mmol) in $CH_2Cl_2$ (70 mL) at −78° C., was added dropwise dimethylsulfoxide (2.89 g, 36.96 mmol). After stirring for 5 minutes, the product of step (c) (5.80 g, 15.4 mmol) in a solution of $CH_2Cl_2$ (7 mL) was added dropwise and the reaction was stirred for 20 minutes at −78° C. Triethylamine (7.78 g, 77 mmol) was then added and the reaction was allowed to warm to room temperature. The mixture was diluted with brine (70 mL) and extracted with $CH_2Cl_2$ (3×70 mL). The combined organic extract was dried with $MgSO_4$ and concentrated. The crude 6.4 was taken up in methanol (80 mL) and Amberlyst-15 ion exchange resin (0.1 g) was added. The mixture was stirred for 2 hours, filtered and concentrated. The resulting solid was crystallized from methanol-hexanes to afford 3.10 g of 6.5.

(e) The intermediate prepared in step (d) was converted by Procedure A to afford 6.6.

(f) The intermediate prepared in step (e) was converted by Procedure B to afford 6.7.

(g) The intermediate prepared in step (f) was converted by Procedure C to afford 6.8. m.p. 101.0–102.5° C.; NMR (300 MHz, DMSO-$d_6$) 1.21–1.44 (14H, m), 1.76-2.00 (2H, m), 4.33 (1H, t, J=4.5 Hz), 5.39 (1H, bt, J=7.5 Hz), 6.39 (2H, bs), 7.30 (3H, m), 7.67 (1H, m), 7.87 (1H, m), 9.24 (1H, s); MS: M+ =351.

Analysis Calc'd for $C_{18}H_{26}N_2O_3S$: C, 61.68; H, 7.48; N, 7.99.

Found: C, 61.25; H, 7.50; N, 8.13.

EXAMPLE 7

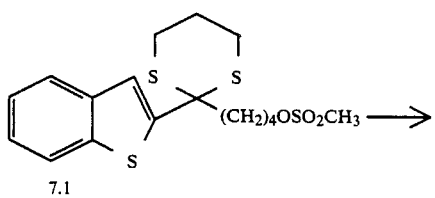
7.1

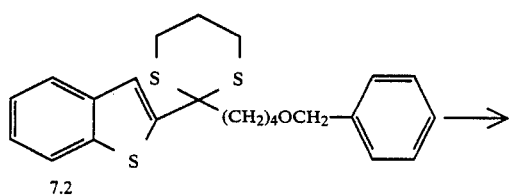
7.2

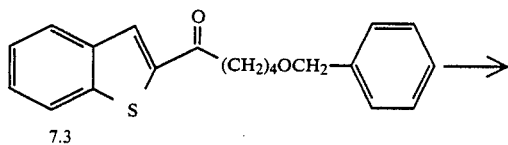
7.3

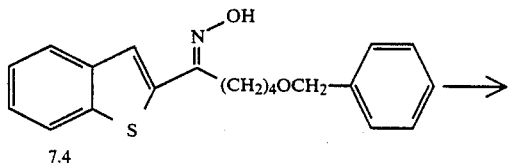
7.4

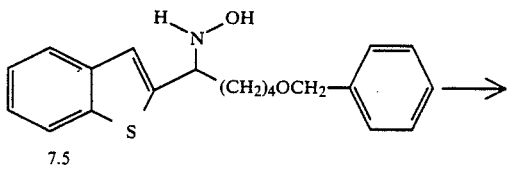
7.5

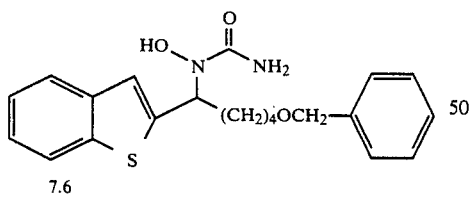
7.6

(a) To a suspension of NaH (478 mg of 60% oil dispersion, 12.0 mmol) in THF (50 mL) was added dropwise benzyl alcohol (1.30 g, 12.0 mmol). After stirring for 5 minutes, 7.1 (4.37 g, 10.9 mmol) in THF (5 mL) was added and the mixture was heated at 50° C. for 3 days. The mixture was diluted with aqueous saturated NH4Cl (50 mL) and extracted with EtOAc (3×50 mL). The combined organic extract was dried with MgSO4 and concentrated. The resulting residue was chromatographed (silica gel, ether-hexanes, 5:95) and afforded 3.91 g of 7.2.

(b) To a stirred suspension of N-bromosuccinimide (11.03 g, 62.2 mmol) in 1.1 CH3CN:H2O (30 mL) at 0° C. was added 80.2 (3.2 g, 7.77 mmol) in CH3CN (5 mL). The mixture was stirred for 5 min. then diluted with aqueous. sat'd NaHCO3 (30 mL) and extracted with EtOAc (3×40 mL). The combined organic extract was dried with MgSO4 and concentrated. The resulting residue was chromatographed (silica gel, ether-hexanes, 4:1) and afforded 7.3.

(c) The intermediate prepared in step (b) was converted by Procedure A to afford 7.4

(d) The intermediate prepared in step (c) was converted by Procedure B to afford 7.5.

(e) The intermediate prepared in step (d) was converted by Procedure C to afford 7.6. m.p. 119.5-120.5° C.; NMR (300 MHz, DMSO-d6) 1.27-1.52 (2H, m), 1.53-1.66 (2H, m), 1.78-2.04 (2H, m), 3.42 (2H, t, J=6 Hz), 4.43 (2H, s), 5.40 (1H, t, J=7 Hz), 6.40 (2H, bs), 7.29 (7H, m), 7.76 (1H, m), 7.88 (1H, m), 9.27 (1H, bs); MS: M+ =385.

Analysis Calc'd for $C_{21}H_{24}N_{22}O_3S$: C, 65.60; H, 6.29; N, 7.29.

Found: C, 65.46; H, 6.45; N, 7.14.

EXAMPLE 8

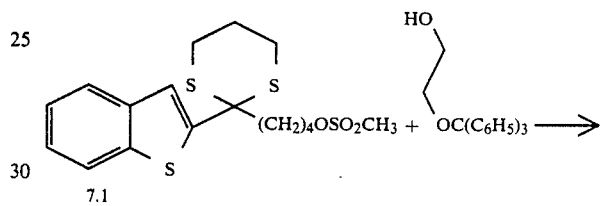
7.1

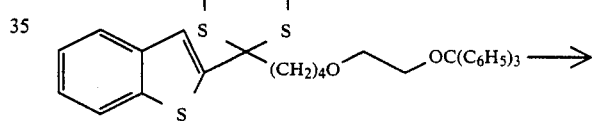
8.2

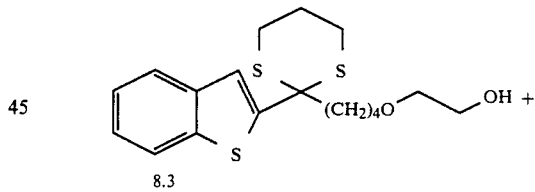
8.3

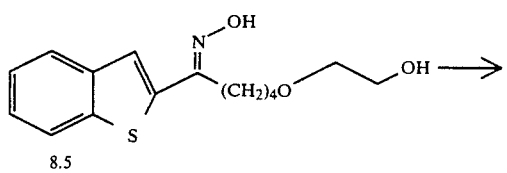
8.4

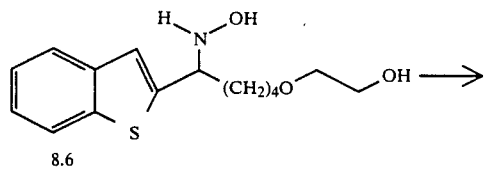
8.5

8.6

-continued

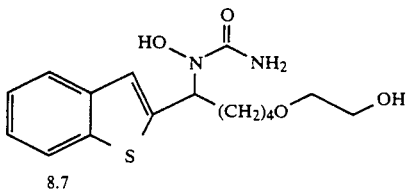
8.7

(a) To a solution of cis 2-butene-1,4-diol (7.06 g, 77.7 mmol) in dichloromethane (300 mL) and THF (30 mL) was added triethylamine (27.0 mL, 194 mmol) followed by triphenylmethylchloride (48.6, 171 mmol). The mixture was stirred for 18 hours and then concentrated in vacuo. Water (200 mL) was added and the mixture was extracted with ether (2×300 mL). The combined organic extract was washed with brine (2×300 mL), dried with MgSO4 and concentrated. Crystallization of the residue from ether, dichloromethane and hexane gave 35.79 g of bis-1,4- triphenylmethoxy-2-butene.

(b) A mixture of ozone and oxygen gas was bubbled through a stirred solution of bis-1,4-triphenylmethoxy-2-butene (8.0 g, 8.73 mmol) in dichloromethane (45 mL) at −78° C. until a blue tint was apparent in the solution. Nitrogen gas was then introduced to remove excess ozone. Dimethyl sulfide (2.95 mL, 55.6 mmol) was added and the mixture was allowed to warm to room temperature for 2 hours. Methanol (25 mL) was added and the mixture was cooled to 0° C. and NaBH4 (330 mg, 8.73 mmol) was added. The mixture was stirred for 1 hour and then water (25 mL) was added and the mixture was evaporated in vacuo to remove the methanol. The resulting solution was diluted with aqueous saturated NH4Cl (25 mL) and extracted with ethyl acetate (1×200 mL). The aqueous solution was acidified to pH 1 with 10% HCl and extracted with ethyl acetate (2×200mL). The combined organic extracts were washed with aqueous saturated NaHCO3, brine, dried with Na2SO4 and concentrated. The resulting residue was chromatographed (silica gel, ethyl acetate-hexanes, gradient 1:9 to 1:1) and afforded 2.52 g of 2-triphenylmethoxy-1-ethanol.

(c) To a stirred solution of 2-triphenylmethoxy-1-ethanol (4.33 g, 14.2 mmol) in THF (70 mL) at 0° C., was added NaH (570 mg of 60% oil dispersion, 14.2 mmol). The solution was allowed to warm to room temperature and 7.1 (5.59 g, 13.92 mmol) in THF (5 mL), was added dropwise and the reaction was brought to reflux for 42 hours. The reaction was then diluted with aqueous saturated NH4Cl (70 mL) and extracted with EtOAc (3×70 mL). The combined organic extract was dried with MgSO4 and concentrated to afford 8.2.

(d) The intermediate from step (c) above was taken up in CH2Cl2 (70 mL) and a catalytic amount of p-toluenesulfonic acid was added. The mixture was stirred for 5 hours, then diluted with aqueous saturated NaHCO3 (70 mL) and extracted with C2CL2 (3×70 mL). The combined organic extract was dried with MgSO4 and concentrated. The resulting residue was chromatographed (silica gel, ether-hexanes, 1.1) afforded 2.85 g of 8.3 along with 660 mg of 8.4.

(e) To a stirred suspension of N-bromosuccinimide (11.03 g, 62 2 mmol) in 1:1 CH3CN:H2O (30 mL) at 0° C. was added 8.3 (2.85 g, 7 77 mmol) in CH3CN (5 mL). The mixture was stirred for 5 minutes, diluted with aqueous saturated NaHCO3 (30 mL) and extracted with EtOAc (3×40 mL). The combined organic extract was dried with MgSO4 and concentrated. The resulting residue was chromatographed (silica gel, ether-hexanes, 4:1) and afforded 8.4 (4.14 g) as a solid. This solid residue was crystallized from CH2Cl2-hexanes to afford 1.49 g of 8.4 as an off-white solid.

(f) The intermediate prepared in step (e) was converted by Procedure A to afford 8.5.

(g) The intermediate prepared in step (f) was converted by Procedure B to afford 8.6.

(h) The intermediate prepared in step (g) was converted by Procedure C to afford 8.7. m.p. 131.5– 132.5° C.; NMR (300 MHz, DMSO-d6) 1.24–1.62 (4H, m), 1.79–2.05 (2H, , 3.37 (4H, m), 3.46 (2H, m), 4.58 (1H, t, J=6 Hz), 5.39 (1H, t, J=7.5 Hz), 6.41 (2H, bs), 7.30 (3H, m), 7.77 (1H, 7.88 (1H, m), 9.27 (1H, bs); Mass spectrum: M+ =339.

Analysis Calc'd for C16H22N2O4S: C, 56.78; H, 6.55; N, 8 28.

Found: C, 56.79; H, 6.48; N, 8.08.

EXAMPLE 9

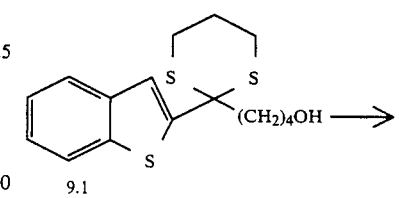
9.1

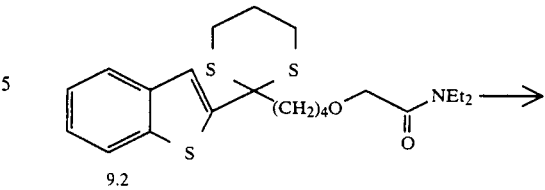
9.2

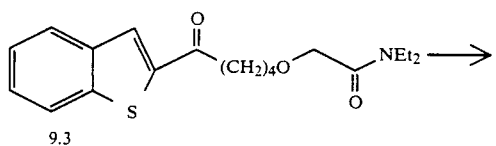
9.3

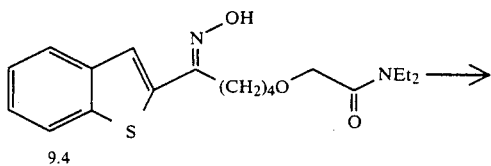
9.4

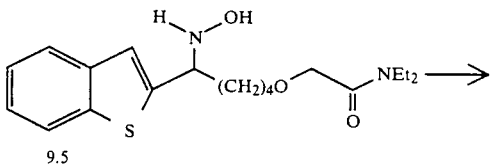
9.5

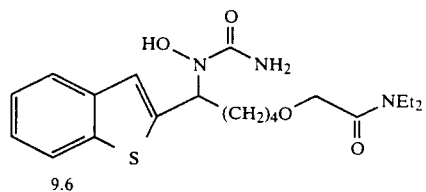
9.6

(a) To a stirred solution of 9.1 (5.47 g, 16.9 mmol) in THF (80 mL) at 0° C. was added NaH (0.71 g of a 60% oil dispersion, 17.7 mmol) and the mixture was stirred for 5 minutes. The cooling bath was withdrawn and a solution of N,N-diethyl-a-bromoacetamide (3.43 g, 17.7 mmol, prepared by the method of W. E. Weaver, W. M. Whaley, J. Am. Chem. Soc. 1947, 69, 515) in THF (5 mL) was added dropwise. The mixture was stirred for 18 hours and then diluted with aqueous saturated NH₄Cl (80 mL) and extracted with EtOAc (3×80 mL). The combined organic extract was dried with MgSO₄ and concentrated. The resulting residue was chromatographed (silica gel, ether:hexanes, 1:1) and afforded 4.12 g of 9.2.

(b) The intermediate prepared in step (a) was converted by the method used in Example 87(c) to afford 9.3.

(c) The intermediate prepared in step (b) was converted by Procedure A to afford 9.4.

(d) The intermediate prepared in step (c) was converted by Procedure B to afford 9.5.

(e) The intermediate prepared by step (d) was converted by Procedure C to afford 9.6. m.p. 125.5–127.5° C.; NMR (300 MHz, DMSO-$d_6$) 0.99 (3H, t, J=7Hz), 1.06 (3H, t, J=7 Hz), 1.24–1.62 (4H, m), 1.80–2.04 (2H, m), 3.22 (4H, q, J=6 Hz), 3.41 (2H, t, J=6 Hz), 4.05 (2H, s), 5.39 (1H, t, J=8 Hz ), 6.40 (2H, bs), 7.31 (3H, m), 7.77 (1H, m), 7.88 (1H, m), 9.27 (1H, bs); MS: M+=408.

Analysis Calc'd for $C_{20}H_{29}N_3O_4S$: C, 58.94; H, 7.17; N, 10.31.

Found: C, 58.83; H, 7.16; N, 10.23.

EXAMPLE 10

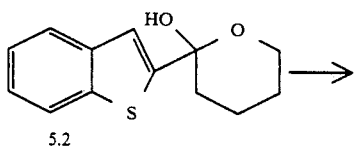
5.2

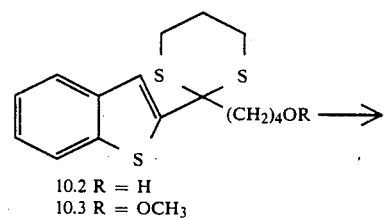
10.2 R = H
10.3 R = OCH₃

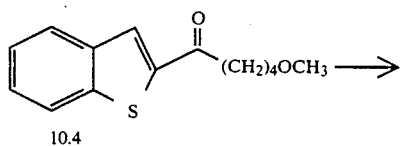
10.4

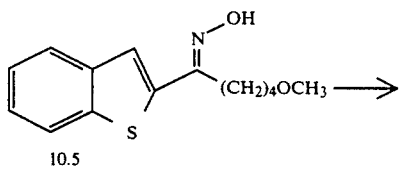
10.5

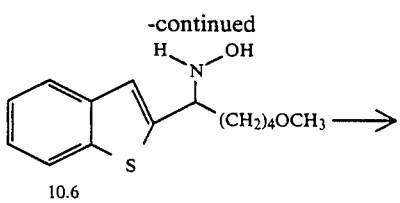
10.6

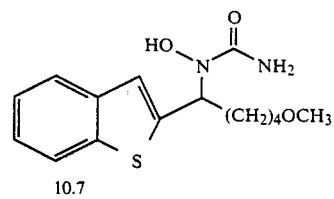
10.7

(a) To a stirred solution of 5.2 (8.87 g, 37.9 mol) in CH₂Cl₂ (200 mL) was added 1,3-propanedithiol (4.56 g, 41.7 mmol) followed by the addition of Amberlyst-15 ion exchange resin (1.0 g). After stirring for 48 hours, the reaction was filtered and concentrated. The resulting residue was purified by column chromatography (silica gel, ether-hexanes, 45:55) and afforded 11.48 g of 10.2 as a clear viscous oil.

(b) To a stirred solution of the product of step (a) (3.03 g, 9.4 mmol) in THF (50 mL) at 0° C. was added NaH (0.39 g of a 60% oil dispersion, 9.8 mmol) and the mixture was stirred for 5 minutes and iodomethane (1.39 g, 9.8 mmol) was then added. The cooling bath was withdrawn and the reaction was stirred at room temperature for 18 hours and then refluxed for 24 hours. More NaH (0.39 g, 9.8 mmol) and iodomethane (1.39 g, 9.8 mmol) was added and the reaction was stirred at room temperature for 2 days. The mixture was diluted with aqueous saturated NH₄Cl (50 mL) and extracted with EtOAc (3×50 mL). The combined organic extract was dried with MgSO₄ and concentrated, to afford 10.3.

(c) A solution of intermediate prepared in step (b) in CH₃CN (5 mL) was added dropwise to an ice cold solution of N-bromosuccinimide (13.38 g, 75.20 mmol) in 80% aqueous CH₃CN (45 mL). After stirring for 5 minutes, the reaction was diluted with aqueous saturated NaHCO₃ (50 mL) and extracted with EtOAc (3×50 mL). The combined organic extract was dried with MgSO₄ and concentrated. The residue was purified by column chromatography (silica gel, ether-hexanes, 1:4) and afforded 1.14 g of 10.4 as an off-white solid.

(d) The intermediate prepared in step (c) was converted by Procedure A to afford 10.5.

(e) The intermediate prepared in step (d) was converted by Procedure B to afford 10.6.

(f) The intermediate prepared in step (e) was converted by Procedure C to afford 10.7. m.p. 135.0–136.0° C.; NMR (300 MHz, DMSO-$d_6$) 1.23–1.60 (4H, m), 1.80–2.04 (2H, m), 3.20 (3H, m), 3.30 (2H, t, J=7.5 Hz), 5.39 (1H, m), 6.38 (2H, bs), 7.31 (3H, m), 7.77 (1H, m), 7.87 (1H, m), 9.25 (1H, s); MS: M+=309.

Analysis Calc'd for $C_{15}H_{20}N_2O_3S$: C, 58.42; H, 6.54; N, 9.09.

Found: C, 58.05; H, 6.53; N, 8.95.

EXAMPLE 11

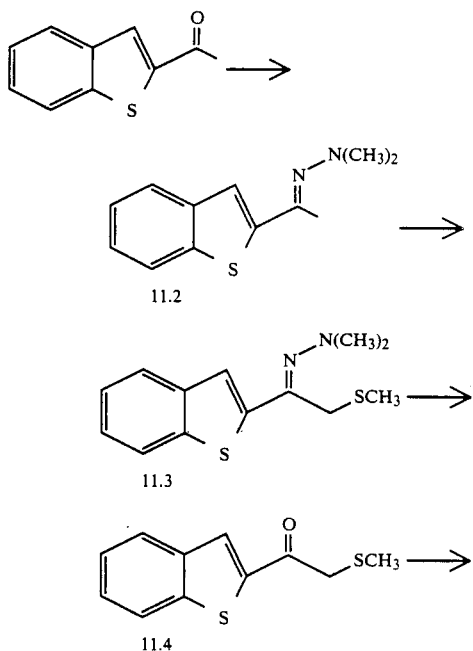

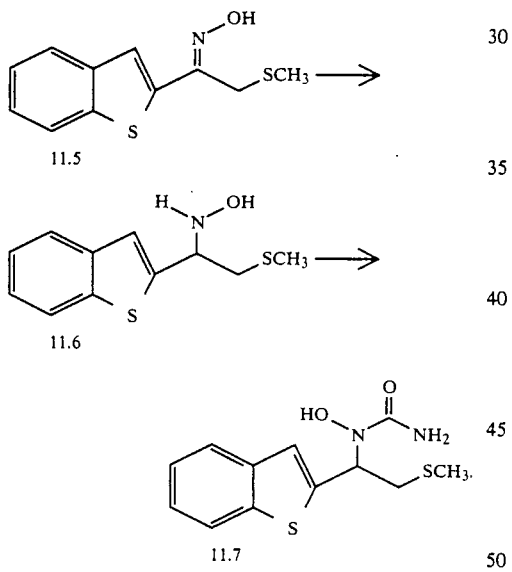

(a) A solution of 2-acetylbenzothiophene (10.00 g, 56.8 mmol) and 1,1-dimethylhydrazine (13.6 g, 227.2 mmol) in ethanol (30 mL) was refluxed for 18 hours and then concentrated in vacuo. The resulting residue was chromatographed (silica gel, ether-hexanes, 1:9) and afforded 9.90 g of 11.2.

(b) To a stirred solution of diisopropylamine (0.46 g, 4.6 mmol) in THF (20 mL) at 0° C., was added dropwise n-BuLi (1.84 mL of 2.5 M, 4.6 mmol). The solution was stirred for 20 minutes and the product of step (a) (1.00 g, 4.6 mmol) in THF (3 mL) was added and the mixture was stirred for 20 minutes at 0° C. The mixture was then cooled to −78° C, and methyldisulfide (0.43 g, 4.6 mmol) was added. After stirring for 1.5 hours at −78° C., the reaction was diluted with aqueous saturated. NH4Cl (20 mL), allowed to warm to room temperature and extracted with EtOAc (3×20 mL). The combined organic extract was dried with MgSO4 and concentrated to afford 11.3.

(c) A solution of the intermediate from step (b) in 105 mL of a standard solution of CuCl2 (standard ratios are as follows: 1.1 mmol CuCl2 in 15 mL THF, 3 mL pH7 buffer, 5 mL H2O) was stirred for 1 hour. The mixture was then concentrated in vacuo to remove the THF and the resulting aqueous solution was extracted with CH2Cl2 (3×80 mL). The combined organic extract was dried with MgSO4 and concentrated. The resulting residue was chromatographed (silica gel, ether:hexanes, 15:85) and afforded 750 mg of 11.4.

(d) The intermediate from step (c) was converted by Procedure A to afford 11.5.

(e) The intermediate from step (d) was converted by Procedure B to afford 11.6.

(f) The intermediate from step (e) was converted by Procedure C to afford 11.7. m.p. 152.5–153.5° C.; NMR (300 MHZ, DMSO-d6) 2.09 (3H, s), 3.03 (2H, ddd), 5.59 (1H, t, J=8 Hz), 6.44 (2H, bs), 7.32 (3H, m), 7.78 (1H, m), 7.89 (1H, m), 9.38 (1H, s); MS: M+ =283.

Analysis Calc'd for $C_{12}H_{14}N_2O_2S_2$: C, 51 04; H, 5.00; N,

Found: C, 50.38; H, 4.95; N, 9.80.

EXAMPLE 12

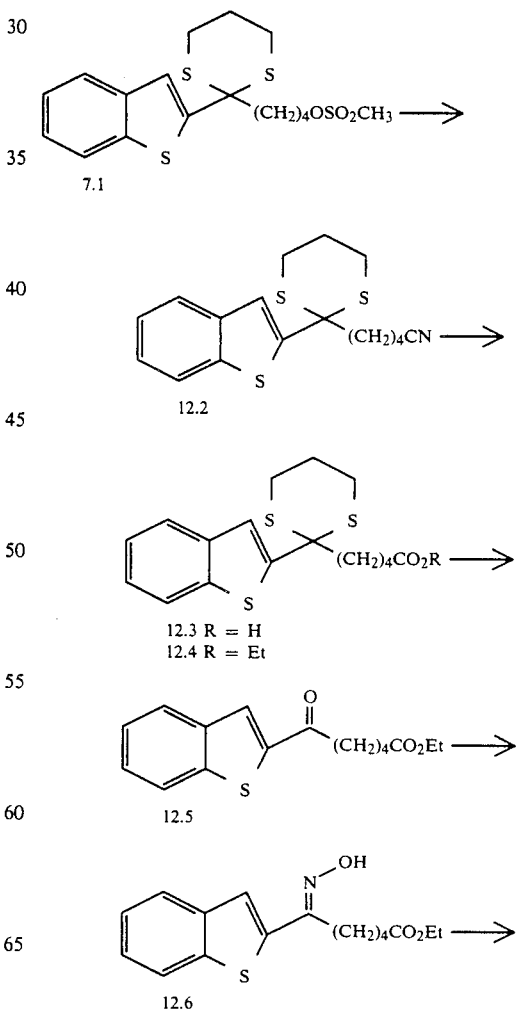

-continued

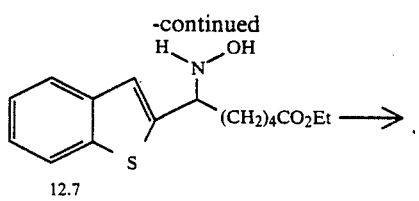
12.7

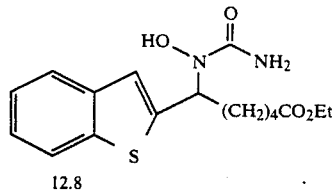
12.8

(a) A solution of 7.1 (15.00 g, 37.3 mmol) and NaCN (1.92 g, 39.2 mmol) in DMSO (150 mL) was heated at 80° C. for 1 hour. The mixture was diluted with brine (100 mL) and extracted with EtOAc (3×100 mL). The combined organic extract was dried with MgSO$_4$ and concentrated. The resulting residue was chromatographed (silica gel, ether:hexanes, 3:7) and afforded 8.56 g of 12.2 as a white solid.

(b) A solution of the product of step (a) (3.85 g, 11.6 mmol) in 1:1 ethylene glycol:40% aqueous KOH (60 mL) was heated at 150° C. for 18 hours. The mixture was then acidified to pH3 with conc. HCl and extracted with EtOAc (3×70 mL). The combined organic extract was dried with MgSO$_4$ and concentrated. The resulting residue was chromatographed (silica gel, ether-hexanes, 1:1) and afforded 2.81 g of 12.3 as a white solid.

(c) A solution of the product of step (b) (2.45 g, 7.0 mmol) in ethanol (40 mL) containing a few drops of H$_2$SO$_4$ to achieve pH4, was refluxed for 2 hours. The reaction was then diluted with brine (40 mL) and extracted with EtOAc (3×40 mL). The combined organic extract was dried with MgSO$_4$ and concentrated. The resulting residue was chromatographed (silica gel, ether:hexanes, 1:9) and afforded 2.58 g of 12.4.

(d) The intermediate of step (c) was converted by the method of Example 83(b) and (c) to afford 12.5.

(e) The intermediate of step (d) was converted by Procedure A to afford 12.6.

(f) The intermediate of step (e) was converted by Procedure B to afford 12.7.

(g) The intermediate of step (f) was converted by Procedure C to afford 12.8. m.p. 144.5–145.0° C.; NMR (300 MHz, DMSO-d$_6$) 1.15 (3H, t, J=7 Hz), 1.22–1.49 (2H, m), 1.58 (2H, m), 1.78–2.03 (2H, m), 2.28 (2H, &, J=7 Hz), 4.03 (2H, q, J=7 Hz), 5.38 (2H, t, J=8 Hz), 6.41 (2H, bs), 7.31 (3H, m), 7.77 (1H, m), 7.88 (1H, m), 9.26 (1H, bs); MS: M+ =351.

Analysis Calc'd for C$_{17}$H$_{22}$N$_2$O$_4$S: C, 58.26; H, 6.33; N,

Found: C, 58.24; H, 6.33; N, 7.91.

EXAMPLE 13

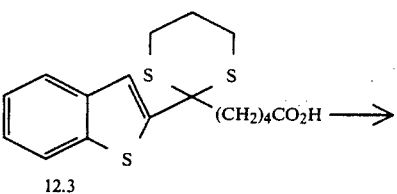
12.3

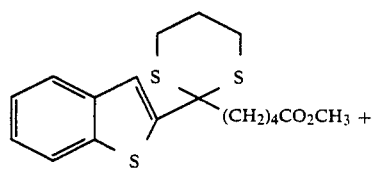
13.2

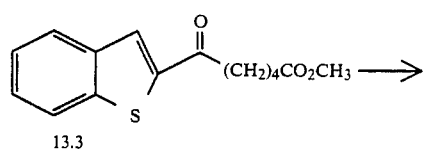
13.3

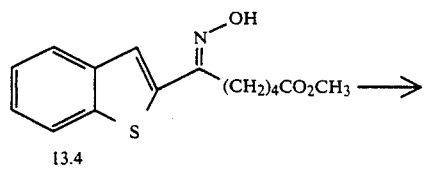
13.4

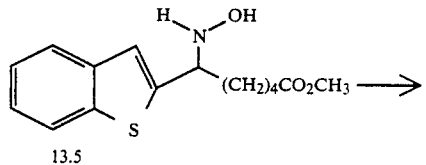
13.5

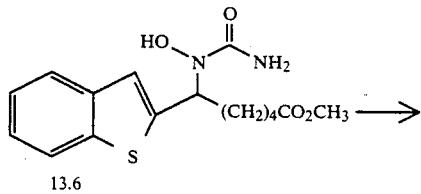
13.6

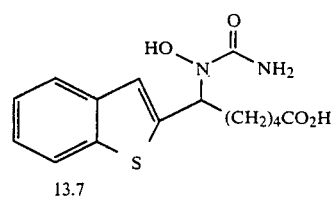
13.7

(a) To a stirred solution of the product of Example 12(b) (20 mmol) in 2:1 CH$_3$CN:H$_2$O (100 mL) containing solid NaHCO$_3$ (0.1 g) was added iodomethane (10 mL) and the reaction was heated for 1 hour at 90° C. The mixture was diluted with aqueous saturated NaHCO$_3$ (60 mL) and extracted with EtOAc (3×100 mL). The combined organic extract was dried with MgSO$_4$ and concentrated. The resulting residue was chromatographed (silica gel, ether-hexanes, 1:4) and afforded 0.31 g of 13.2 along with 2.57 g of 13.3.

(b) The intermediate 99 was converted by Procedure A to afford 13.4.

(c) The intermediate of step (b) was converted by Procedure B to afford 13.4.

(d) The intermediate of step (c) was converted by Procedure C to afford 13.6.

(e) To a stirred solution of the product of step (d) (0.41 g, 1.22 mmol) in isopropanol (6 mL) was added LiOH H$_2$O (128 mg, 3.06 mmol) and 4 drops of H$_2$O. The reaction was stirred for 18 hours, concentrated and the resulting residue was taken up in brine (4 mL) and washed with ethyl acetate (2×). The aqueous layer was acidified with conc. HCl and extracted with ethyl acetate (3×10 mL). The combined organic extract was dried with MgSO₄ and concentrated. Crystallization from MeOH-hexanes afforded 13.7. m.p. 151° C. (dec); NMR (300 MHz, DMSO-d₆) 1.28 (2H, m), 1.41 (2H, m), 1.55 (2H, m), 1.78-1.97 (2H, m), 2.20 (2H, t, J=7.5 Hz), 5.39 (1H, t, J=7.5 Hz), 6.41 (2H, bs), 7.31 (3H, m), 7.77 (1H, m), 7.88 (1H, m), 9.27 (1H, bs), 12.00 (1H, bs); MS: M⁺323.

Analysis Calc'd for C₁₅H₁₈N₂O₄S: C, 55.88; H, 5.63; N, 8.69.

Found: C, 55.29; H, 5.57; N, 8.41.

EXAMPLE 14

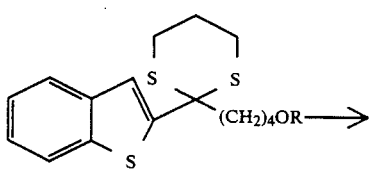

9.1 R = H
7.1 R = OSO₂CH₃

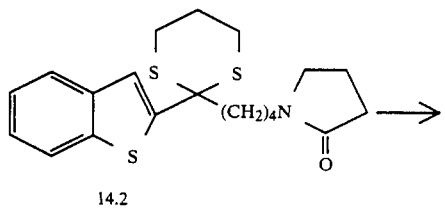

14.2

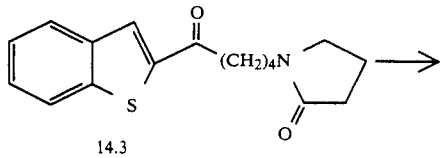

14.3

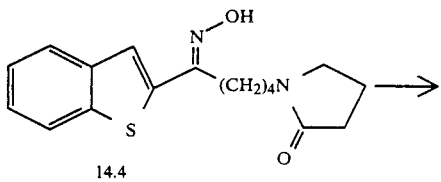

14.4

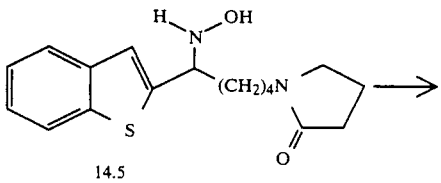

14.5

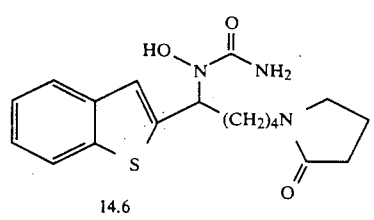

14.6

(a) To a stirred solution of 9.1 (1.02 g, 3.1 mmol) and triethylamine (344 mg, 3.41 mmol) in CH₂Cl₂ (15 mL) at 0° C. was added methanesulfonyl chloride (379 mg, 3.3 mmol). The cooling bath was withdrawn and the reaction mixture was allowed to stir for 10 minutes. The mixture was diluted with brine (15 mL) and extracted with EtOAc (3×15 mL). The combined organic extract was dried with MgSO₄ and concentrated. The crude residue was triturated with ether and the triethylamine hydrochloride was filtered off. The filtrate was concentrated to afford 7.1.

(b) To a stirred suspension of NaH (588 mg of 60% oil dispersion, 14.7 mmol) in THF (70 mL) was added 2-pyrrolidinone (1.25 g, 14.7 mmol). After all evolution of gas had ceased, the product of step (a) (5.63 g, 14.0 mmol) in THF (5 mL) was added dropwise. The reaction was brought to reflux for 18 hours and then diluted with aqueous saturated NH₄Cl (70 mL) and extracted with EtOAc (3×70 mL). The combined organic extract was dried with MgSO₄ and concentrated. The resulting residue was chromatographed (silica gel, ether) and afforded 4.83 g of 14.2.

(c) A stirred solution of the product of step (b) (4.03 g, 10.3 mmol) and iodomethane (29 g, 0.20 mol) in 2:1 CH₃CN:H₂O (50 mL) containing solid Na₂CO₃ (1.0 g) was refluxed for 18 hours. The reaction was then diluted with aqueous saturated NaHCO₃ (50 mL) and extracted with EtOAc (3x50 mL). The combined organic extract was dried with MgSO₄ and concentrated. The resulting residue was chromatographed (silica gel, ether:methanol, 96:4) and afforded 2.06 g of 14.3 as a white solid.

(d) The intermediate of step (c) was converted by Procedure A to afford 14.4.

(e) The intermediate of step (d) was converted by Procedure B to afford 14.5.

(f) The intermediate of step (e) was converted by Procedure C to afford 14.6. m.p. 142.5-143.5 C; NMR (300 MHz, DMSO-d₆) 1.15-1.58 (4H, m), 1.79-2.06 (4H, m), 2.18 (2H, t, J=8 Hz), 3.16 (2H, t, J=7 Hz), 3.29 (2H, t, J=7 Hz), 5.38 (1H, dd, J=6 Hz), 6.41 (2H, bs), 7.29 (3H, m) 7.77 (1H, m), 7.88 (1H, m), 9.26 (1H, bs); MS: M⁺=362.

Analysis Calc'd for C₁₈H₂₃N₆O₃S: C, 59.81; H, 6.41; N, 11.63.

Found: C, 59.21; H, 6.53; N, 12.04.

EXAMPLE 15

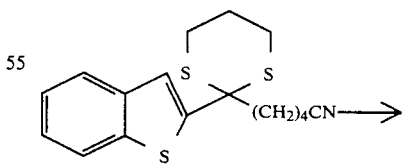

12.2

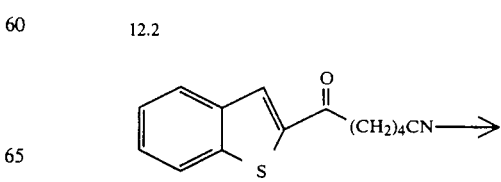

15.2

-continued

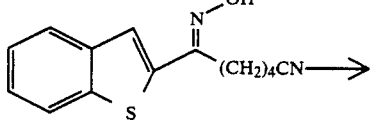
15.3

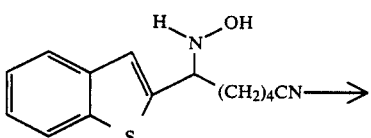
15.4

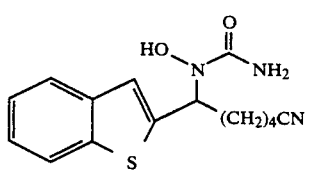
15.5

(a) To a stirred solution of the product 12.2 (7.98 g, 24 mmol) in 2:1 CH$_3$CN:H$_2$O (120 mL) containing solid Na$_2$CO$_3$ (1.0 g) was added iodomethane (34 g, 0.24 mol) and this mixture was heated at 90° C. for 18 hours. The mixture was diluted with aqueous saturated NaHCO$_3$ (120 mL) and extracted with ethyl acetate (3×120 mL). The combined organic extract was dried with MgSO$_4$ and concentrated. The resulting residue was chromatographed (silica gel, ether-hexanes, 3:7) and afforded 4.68 g of 15.2 as a white solid.

(b) The intermediate of step (a) was converted by Procedure A to afford 15.3.

(c) The intermediate of step (b) was converted by Procedure B to afford 15.4.

(d) The intermediate of step (c) was converted by Procedure C to afford 15.5. m.p. 169–170° C.; NMR (300 MHz, DMSO-d$_6$) 1.29–1.67 (4H, m), 1.79–2.06 (2H, m), 2.50 (2H, t, under DMSO), 5.41 (1H, dd, J =6 Hz), 6.44 (2H, bs), 7.30 (3H, m), 7.77 (1H, m), 7.88 (1H, m), 9.30 (1H, s); MS: M+ =304.

Analysis Calc'd for C$_{15}$H$_{17}$N$_3$O$_2$S: C, 59.38; H, 5.65; N, 13.85.

Found: C, 59.11; H, 5.66; N, 13.78.

EXAMPLE 16

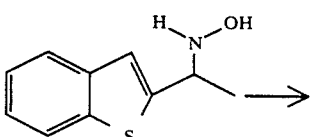
2.1

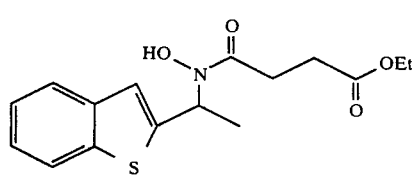
16

To a solution of N-(1(2- benz[b]thienyl)ethyl)- hydroxylamine (2.0 g, 10.35 mmol) in methylene chloride (60 mL) at 0–4° C., under nitrogen was added triethylamine (1.52 mL, 10.87 mmol) followed by trimethylsilylchloride (1.31 mL, 10.35 mmol). The mixture was stirred for 30 minutes at 0–4° C. then 24 hours at room temperature. The reaction was cooled to 0–4° C. and diisopropylethylamine (1.98 mL, 11. 4 mmol) and ethyl succinylchloride (1.61 mL, 10.87 mmol) were added sequentially. The reaction was stirred 15 minutes at 0–4° C. then 30 minutes at room temperature before diluting into 25 mL of 10% HCl and extracting with ethyl acetate (2×100 mL). The combined organic extract was washed with aqueous saturated NaHCO$_3$, H$_2$O, and brine, dried with Na$_2$SO$_4$ and concentrated in vacuo to afford a yellow solid which upon purification by chromatography (silica gel, ethyl acetate-hexanes) yielded 1.63 g of desired product 16. m.p. 96.3–97.6° C.; NMR (300 MHz, DMSO-d$_6$): 1.18 (3H, t); 1.58 (3H, d); 2.5 (2H, m); 2.68 (2H, m); 4.05 (2H, q); 5.87 (1H, q); 7.28–7.38 (3H, m); 7.8 (1H, m); 7.9 (1H, m); 9.73 (1H, bs); MS: (M+H)+ =322.

Analysis Calc'd for C$_{16}$H$_{19}$NO$_4$S: C, 59.79; H, 5.96; N 4.36.

Found: C, 59 41; H, 5.99; N, 4.28.

EXAMPLE 17

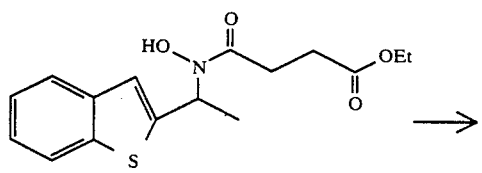
16

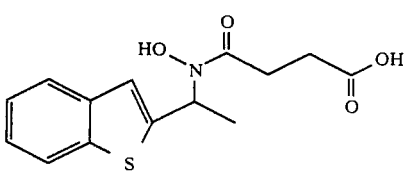
17

To a solution of 16 (1.25 g, 3.89 mmol) in THF (15 mL) was added a solution of LiOH H$_2$O (700 mg, 15.6 mmol) in H$_2$O (10 mL). The mixture was stirred 3 hours and 10% HCl was added to adjust the pH to 1. The resulting mixture was extracted with ethyl acetate (2×100 mL) and the combined organic extract was washed with brine dried with Na$_2$SO$_4$, and concentrated in vacuo. Crystallization from EtOAc/MeOH gave the desired product 17. m.p. 161.5–162.3° C.; NMR (300 MHz, DMSO-d$_6$): 1.58 (3H, d), 2.4–2.5 (2H, m), 2.6–2.75 (2H, m), 5.87 (1H, q), 7.28–7.38 (3H, m), 7.8 (1H, m), 7.9 (1H, m), 9.73 (1H, bs), 12.1 (1H, bs); MS: (M+H)+ =294.

Analysis Calc'd for C$_{14}$H$_{15}$NOhd 4S: C, 57.32; H, 5.15; N, 30 4.77.

Found: C, 56.98; H, 5.22; N, 4.62.

EXAMPLE 18

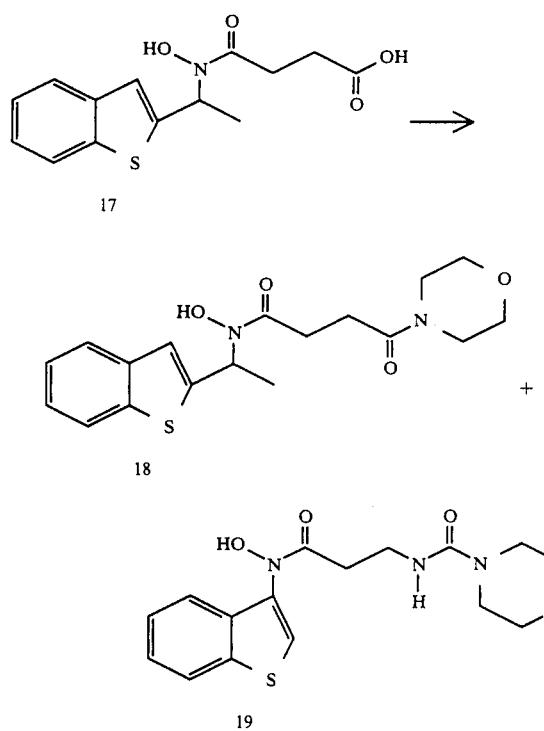

17

18

19

To a stirred solution of the product of Example 17 (800 mg, 2.73 mmol) in benzene (15 mL) was added triethylamine (0.38 mL, 2.73 mmol) and diphenylphosphoryl azide (0.60 mL, 2.73 mmol). The mixture was heated to 80° C. for 1 hour after which morpholine (0.72 mL, 8.19 mmol) was added and the reaction stirred at 80° C. for 23 hours. The mixture was cooled to room temperature, poured into 10% HCl, and extracted with ethyl acetate (2×100 mL). The combined organic extract was washed with aqueous saturated NaHCO₃ and brine, dried with MgSO₄ and concentrated in vacuo to yield a yellow solid. This crude material was purified by chromatography (silica gel, EtOAc-methanol) followed by recrystallization from CH₂Cl₂-hexanes to yield 469 mg of 18 as a white solid. m.p. 75.3–77.3° C.; NMR (300 MHz, DMSO-d₆): 1.58 (3H, d), 2.55–2.8 (4H, m), 3.4–3.6 (8H, m), 5.87 (1H, q), 7.28–7.38 (3H, m), 7.8 (1H, m), 7.9 (1H, m), 9.73 (1H, bs); MS: $(M+H)^+ = 363$.

Analysis Calc'd for $C_{18}H_{22}N_2O_4S(0.75H_2O)$: C, 57.51; H, 6.30; N, 7.45.

Found: C, 57.50; H, 6.02; N, 7.33.

EXAMPLE 19

Compound 19 was isolated as a minor product in the procedure described for Example 18. Recrystallization from CH₂Cl₂-hexanes afforded 81 mg of 19 as a white solid. m.p. 114.1–115.3° C.; NMR (300 MHz, DMSO-d₆): 1.58 (3H, d), 2.58 (2H, t), 3.18–3.22 (4H, m), 3.2–3.3 (2H, m), 3.5 (4H, m), 5.90 (1H, q), 6.55 (1H, t), 7.28–7.38 (3H, m), 7.8 (1H, m), 7.9 (1H, m), 9.68 (1H, bs); MS; $(M+H)^+ = 378$.

Analysis Calc'd for $C_{18}H_{23}N_3O_4S$: C, 57.28; H, 6.14; N, 11.13.

Found: C, 56.93; H, 6.21; N, 10.82.

EXAMPLE 20

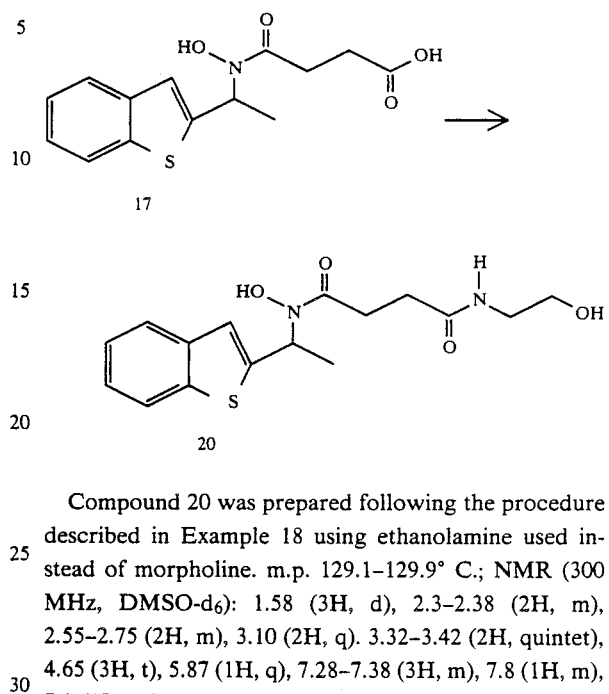

17

20

Compound 20 was prepared following the procedure described in Example 18 using ethanolamine used instead of morpholine. m.p. 129.1–129.9° C.; NMR (300 MHz, DMSO-d₆): 1.58 (3H, d), 2.3–2.38 (2H, m), 2.55–2.75 (2H, m), 3.10 (2H, q). 3.32–3.42 (2H, quintet), 4.65 (3H, t), 5.87 (1H, q), 7.28–7.38 (3H, m), 7.8 (1H, m), 7.9 (1H, m), 9.63 (1H, bs); MS: $(M+H)^+ = 337$.

Analysis Calc'd for $C_{16}H_2.N_2O_4S$: C, 57.13; H, 5.99; N, 8.33.

Found: C, 56.71; H, 6.05; N, 8 18.

EXAMPLE 21

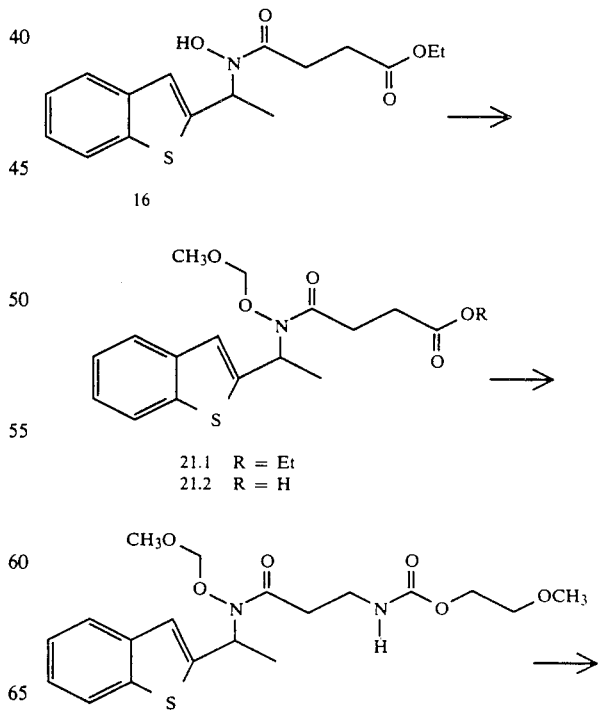

16

21.1  R = Et
21.2  R = H 21.3

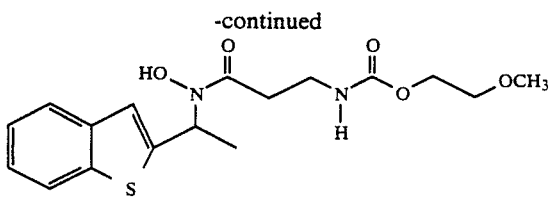

21.4

(a) Chloromethyl methyl ether (2.0 mL, 26.3 mmol) and diisopropylethylamine (4.63 mL, 26.3 mmol) was added to a stirred solution of the product of Example 16 (4.23 g, 13.1 mmol) in methylene chloride (50 mL). The mixture was stirred for 4 hours and then diluted with 10% HCl and extracted with ethyl acetate (2×250 mL). The combined organic extract was washed with saturated aqueous NaHCO₃, H₂O and brine, dried with MgSO₄, concentrated in vacuo and purified by chromatography (silica gel, gradient of ethyl acetate- hexanes)- :to yield 4.46 g of 21.1.

(b) Utilizing the procedure of Example 17, the product of step (a) (4.31 g, 11.8 mmols) was saponified to the acid 21.2 (3.89 g ).

(c) Utilizing the procedure of Example 18, the product of step (b) (1.0 g, 2.96 mmol) was converted to 21.3. Purification by chromatography (silica gel, 30% ethyl acetate-hexanes) afforded 577 mg of 21.3.

(d) A solution of 4.8M HCl in dioxane (2 mL, 9.6 mmol) and 1,3-propanediol (0.50 mL, 6.9 mmol) was added to the product of step (c) (330 mg, 0.80 mmol) and the mixture stirred at room temperature. After 1 hour, the reaction mixture was diluted with H₂O (25 mL) and extracted with ethyl acetate (2×100 mL). The combined organic extract was washed with saturated aqueous NaHCO₃, H₂O and brine, dried with MgSO₄ and concentrated in vacuo. Recrystallization from methylene chloride hexanes gave 186 mg of 21.4. m.p. 79–81 C; NMR (300 MHz, DMSO-d₆): 1.58 (3H, d), 2.52–2.65 (2H, m), 3.15–3.22 (2H, m), 3.22 (3H, s), 3.47 (2H, ), 4.05 (2H, m), 5.88 (1H, q), 7.18 (1H, bt), 7.28–7.38 (3H, m), 7.8 (1H, m), 7.9 (1H, m), 9.72 (1H, bs); MS: (M+H)⁺ =367.

Analysis Calc'd for C₁₇H₂₂N₂O₅S(0.25H₂O): C, 55.05; H, 6.11: N, 7.55.

Found: C, 55.17; H, 6.02; N, 7.55.

EXAMPLE 22

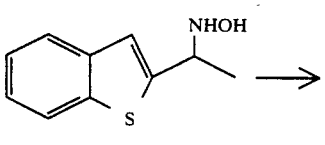

2.1

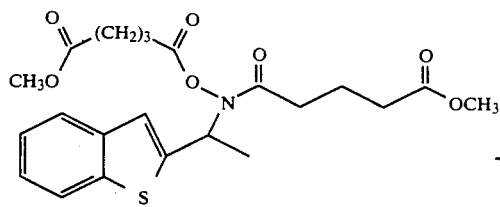

22.1

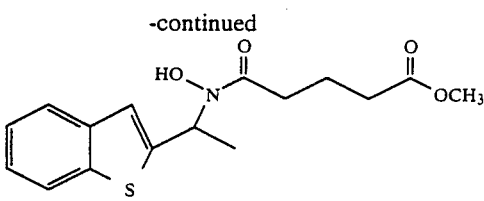

22.2

(a) A suspension of N-(1-(2-benzo[b]thienyl)ethyl)-hydroxylamine (1.02 g, 5.28 mmol) in methylene chloride (25 mL) was cooled to 0° C. and methyl glutarylchoride (1.46 mL, 10.6 mmol) and N,N-diisopropylethylamine (2.75 mL, 15.8 mmol) were added. The mixture was stirred at 0–4° C. for 45 minutes, then at room temperature for 1 hour. The mixture was poured into 10% HCl and extracted with ethyl acetate (2×100 mL). The combined organic extract was washed with brine, dried with MgSO₄, filtered and concentrated in vacuo to yield 2.51 g of a yellow syrup. Chromatography (silica gel, 30% ethyl acetate-hexanes) yielded 1.77g of the bis-acylation product, 22.1.

(b) Sodium methoxide (220 mg, 4.06 mmol) in MeOH (25 mL) was added to the product of step (a) (1.66g, 3.69 mmol), the mixture was stirred for 2 hours and then 10% HCl was added until the reaction pH was 1. This solution was concentrated in vacuo to remove most of the MeOH. The concentrate was diluted with H₂O (25 mL) and extracted with ethyl acetate (2×100 mL). The combined organic extract was washed with saturated aqueous NaHCO₃, H₂O and brine, dried with MgSO-4and concentrated in vacuo to yield 1.15 g of an off-white solid. Recrystallization from CH₂Cl₂-hexanes gave 1.0 g of the desired product 22.2. m.p. 89.6–91.3° C.; NMR (300 MHZ, DMSO-d₆) 1.58 (3 H, d), 1.75 (2H, q), 2.35 (2H, t), 2.45 (2H, t), 3.6 (3H, s), 5.9 (1H, q), 7.4–7.3 (3H, m), 7.8 (1H, m), 7.9 (1H, m), 9.68 (1H, bs); MS: (M+H)⁺=322.

Analysis Calc'd for C₁₆H₁₉NO₄S: C, 59.79; H, 5.96; N, 4.36.

Found: C, 59.68; H, 5.90; N, 4.32.

EXAMPLE 23

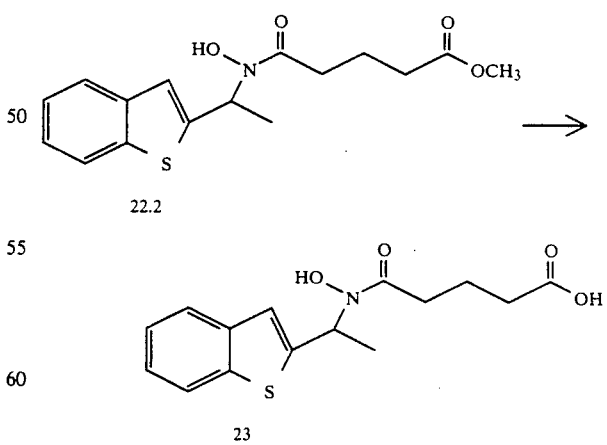

22.2

23

The product 22.2 (606 mg, 1.89 mmol) was dissolved in THF 12 mL) and LiOH (240mg, 5.66 mmol) in 6 ml of H₂O was added and the mixture stirred at room temperature for 3 hours. Aqueous 10% HCl was added to adjust the mixture to pH 1. The mixture was extracted with ethyl acetate (2×100 mL). The combined organic extract was washed with brine (1×50 mL), dried with MgSO4 and concentrated in vacuo to provide 580 mg of a yellowish solid. Recrystallization from ethyl acetate-hexanes gave 406 mg of 23. m.p. 136.5-137.3 C; NMR (300 MHZ, DMSO-d6) 1.58 (3H, d), 1.75 (2H, q), 2.25 (2H, t), 2.43 (2H, t), 5.9 (1H, q), 7.4-7.28 (3H, m), 7 8 (1H, m), 7.9 (1H, m), 9.65 (1H, bs), 12.05 (1H, bs); MS: (M+H)+ =308.

Analysis Calc d for C15H17NO4S: C, 58.62; H, 5.57; N, 4.56.

Found C, 58.17; H, 5.58; N, 4.50.

EXAMPLE 24

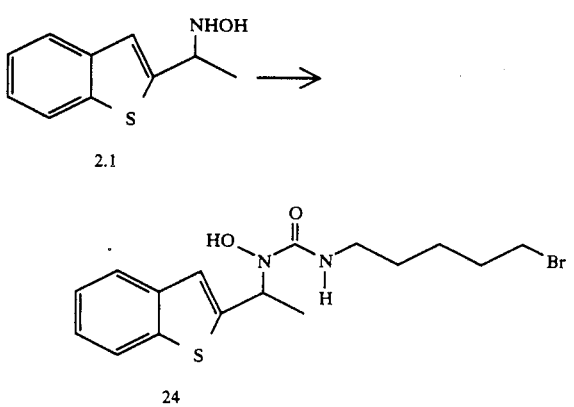

To a stirred solution of N-(1-(2-benzo[b]thienyl-)ethyl) hydroxylamine (12.0g, 62.mmol) in dry THF (40 mL) was added dropwise 5-bromopentylisocyanate (12.05 g, 62.74 mmol) under nitrogen. After 1 hour, the reaction was diluted with EtOAc (200 mL) and was washed with 10% aqueous citric acid (120 mL). The aqueous layer was extracted with EtOAc (50 mL) and the combined organic portion was dried (MgSO4), filtered and concentrated. The dark concentrate yielded 4.51 g of large amber crystals of desired product. The mother liquor was chromatographed (silica gel, EtOAc-hexane, 20:80, 30:70, 40:60, 50:50). Fractions containing pure product were concentrated to provide 9.46 g of additional product 24. m.p. 105-107° C; NMR (300 MHz, DMSO- d6) 1.31 (m, 2), 1.40 (m, 2), 1.51 (d, 3, J=7.0), 1.75 (m, 2), 3.04 (q, 2, J=6.4), 3.45 (t, 2, J=6.6), 5.54 (q, 1, J=7.0), 7.05 (t, 1, J=5.9, NH), 7.25 (br s, 1), 7.3(m, 2), 7.71 (m, 1), 7.87 (m, 1), 9.19 (s, 1, OH); MS: (M+1)+ =387.

EXAMPLE 25

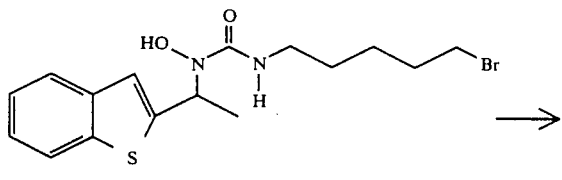

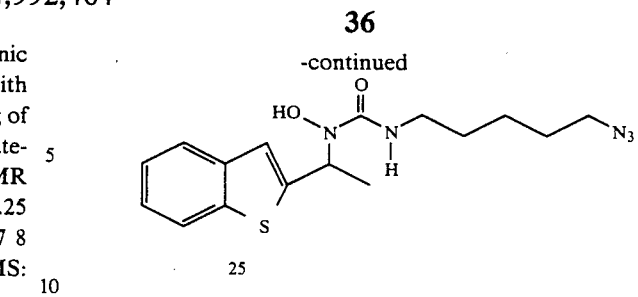

To a stirred solution of the product of Example 24 (3.85 g, 10.0 mmol) in dimethylformamide (10 mL) was added sodium azide (2.15 g, 33.1 mmol) and the reaction was stirred at room temperature under nitrogen for 24 hours. The reaction was diluted with water (150 mL) and was extracted with ethyl acetate (3×100 mL). The extracts were dried with MgSO4, filtered and concentrated. The dark syrup was chromatographed (silica gel, ethyl acetate-hexane, 20:80, 30:70, 40:60). Crystallization from EtOAc-hexane afforded 3.40 g of the desired product 25. m.p. 92-94° C.; NMR (300 MHz, DMSO-d6) 1.23 (m, 2), 1,40 (m, 2), 1.47 (m, 2), 1.51 (d, 3, J=7.0), 3.04 (q, 2, J=6.6), 3.23 (t, 2, J=6.8), 5.54 (q, 1, J=7.0), 7.04 (t, 1, J=6.0, NH), 7.25 (br s, 1), 7.31 (m, 2), 7.76 (dm, 1, J=8.1), 7.87 (dm, 1, J=8.1), 9.19 (s, 1, OH); MS: (M+1)+ =348.

Analysis Calc'd for C16H21N5O2S: C, 55.31; H, 6.09; N,20.16.

Found: C, 55.20; H, 6.01; N, 19.95.

EXAMPLE 26

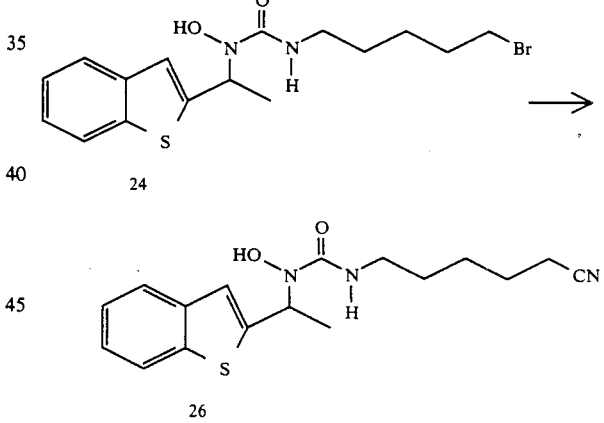

To a stirred solution of the product of Example 24 (3.57 g, 10.0 mmol) in dry DMSO (10 mL) was added sodium cyanide (1.21 g, 24.7 mmol) and the thick amber solution was stirred under nitrogen for 24 hours. After dilution with water (35 mL) and saturated aqueous NaCl (50 mL), the mixture was extracted with ethyl acetate (3×75 mL). The extracts were dried with Na2SO4, filtered and concentrated to give an amber oil. Chromatography (silica gel, ethyl acetate-hexane, 40:60, 0:50) followed by crystallization from ethyl acetate gave 1.95 g of desired product 26. m.p. 107-109° C.; NMR (300 MHz, DMSO-d6) 1.28 (m, 2), 1.38 (m, 2), 1.48 (m, 2), 1.51 (d, 3, J=7.0), 2.39 (t, 2, J=7.0), 3.04 (q, 2, J=6.6), 5.54 (q, 1, J=7.0), 7.06 (t, 1, J=5.9), 7.26 (br s, 1), 7.31 (m, 2), 7.76 (m, 1), 7.87 (m, 1), 9.19 (s, 1, OH); MS: (M+1)+ =332.

Analysis Calc'd for C17H21N3O2S: C, 61.61; H, 6.39; N, 2.68.

EXAMPLE 27

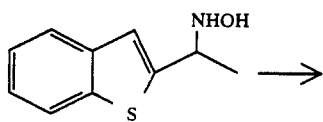

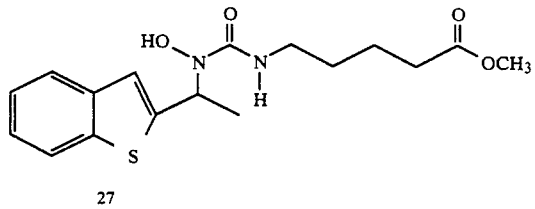

To a stirred solution of adipic acid monomethyl ester (1.76 g, 11.0 mmol) and triethylamine (1.16 g, 11.5 mmol) in dry benzene (40 mL) was added phosphorylazide (3.02 g, 11.0 mmol) under dry nitrogen and the solution was heated at reflux for 1 hour. The solution was allowed to cool to about 35° C., then a solution of N-(1-(2-benzo[b]thienyl)ethyl) hydroxylamine (1.93 g, 10.0 mmol) in dry THF 10 mL) was added. After 1 hour, the solution was added to 100mL of 10% aqueous citric acid and extracted with ethyl acetate (2×100 mL). The extracts were dried with MgSO4, filtered and concentrated and the crude product was chromatographed (silica gel, EtOAc-hexane, 20:80, 30:70, 40:60). Crystallization from EtOAc-hexane gave 2.68 g of desired product 27. m.p. 106.5–108° C.; NMR (300 MHz, DMSO-d6) 1.44 (m, 4), 1.51 (d, 3, J=7.0), 2.28 (t, 2, J=7.2), 3.04 (m, 2), 3.57 (s,3), 5.54 (q, 1, J=7.0), 7.06 (t, 1, J=6.1, NH), 7.25 (br s, 1), 7.31 (m, 2), 7.76 (m, 1), 7.87 (m, 1), 9.18 (s, 1, OH); MS: (M+1)+ =351.

Analysis Calc'd for $C_{17}H_{22}N_2O_4S$: C,58.27; H, 6.33; N, 7.99.

Found: C, 58.18; H, 6.30; N, 7.95.

EXAMPLE 28

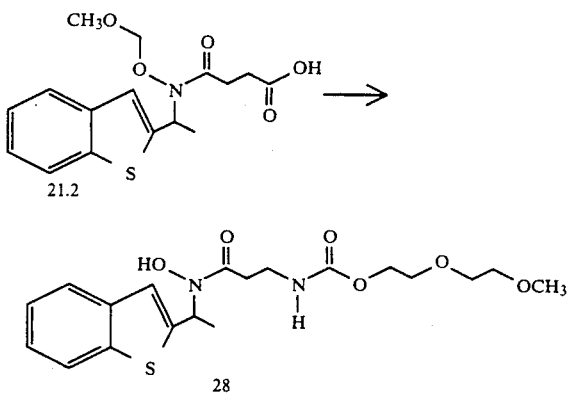

The desired product 28 was prepared by the method of Example 21(c) and (d) from the product of Example 2I(b) using 2-(2-methoxyethoxy)ethanol instead of morpholine. m.p. 50.5–52.0° C.; NMR 300 MHz, DMSO-d6): 1.58 (3H, m), 2.58 (2H, m), 3.2 (2H, m), 3.25 (3H, s), 3.42 (2H, m), 3.5–3.58 (4H, m), 4.05 (2H, m), 5.9 (1H, bq), 7.18 (1H, bt), 7.28–7.38 (3H, m), 7.8 (1H, m), 7.9 (1H, m), 9.7 (1H, bs); MS: (M+H)+ =411.

Analysis Calc'd for $C_{19}H_{26}N_2O_6S$·0.25 mol $H_2O$: C, 54.99; H, 6.44; N, 6.75.

Found: C, 55.02; H, 6.28; N, 6.71.

EXAMPLE 29

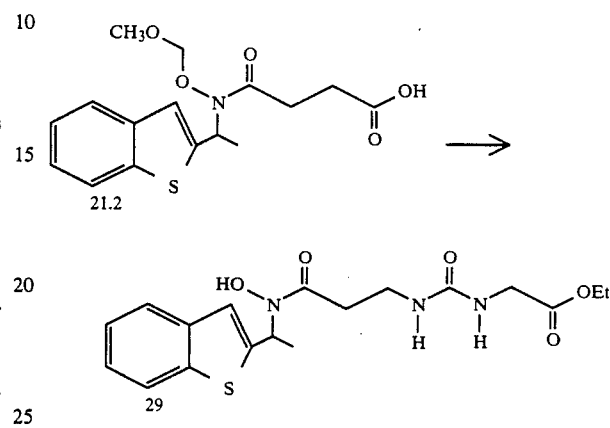

The desired product 29 was prepared by the method of Example 21(c) and (d) from the product of Example 21(b) using glycine ethyl ester HCl salt instead of morpholine. m.p. 154.9–156° C.; NMR (300 MHz, DMSO-d6): 1.18 (3H, t), 1.58 (3H, d), 2.55 (2H, m), 3.35 (2H, m), 3.75 (2H, d), 4.08 (2H, q), 5.9 (1H, bq), 6.2 (1H, bt) 6.35 (1H, bt), 7.28–7.38 (3H, m), 7.8 (1H, m), 7.9 (1H, m), 9.6 (1H, bs); MS: (M+H)+ =394.

Analysis Calc'd for $C_{18}H_{23}N_3O_5S$: C, 54.95; H, 5.89; N, 10.68.

Found: C, 54.68; H, 5.66; N, 10.61.

EXAMPLE 30

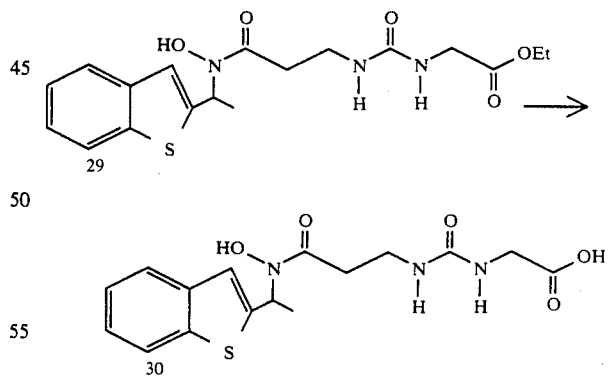

The desired product 30 was prepared by the method of Example 23 from 29. m.p. 185.5–186.4° C.; NMR (300 MHz, DMSO-d6): 1.58 (3H, d), 2.55 (2H, m), 3.25 (2H, q), 3.68 (2H, d), 5.9 (1H, bq), 6.18 (1H, bt), 6.28 (1H, bt), 7.25–7.38 (3H, m), 7.8 (1H, m), 7.9 (1H, m), 9.7 (1H, bs) 12.4 (1H, bs).

Analysis Calc'd for $C_{16}H_{19}N_3O_5S$: C, 52.59; H, 5.24; N, 11.50.

Found: C, 52.62; H, 5.28; N, 11.31.

EXAMPLE 31

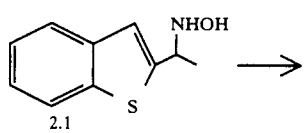

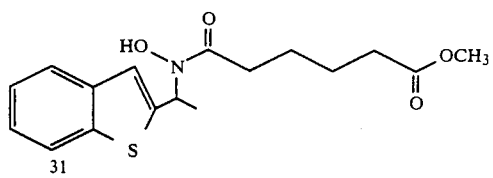

The desired product 31 was prepared by the method of Example 22 from 2.1 using methyl adipyl chloride instead of methyl glutaryl chloride. m.p. 78.5–81.3° C.; NMR (300 MHz, DMSO-d$_6$): 1.55 (7H, m), 2.3 (2H, bt), 2.4 (2H, bt), 3.58 (3H, s), 5.9 (1H, bq), 7.28–7.38 (3H, m), 7.8 (1H, m), 7.9 (1H, m), 9.63 (1H, bs); MS (M+H)+ =336.

Analysis Calc'd for C$_{17}$H$_{21}$NO$_4$S: C, 60.88; H, 6.31; N, 4.18.

Found: C, 60.89; H, 6.40; N, 4.16.

EXAMPLE 32

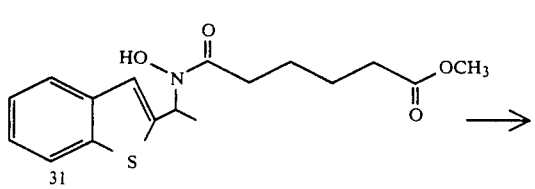

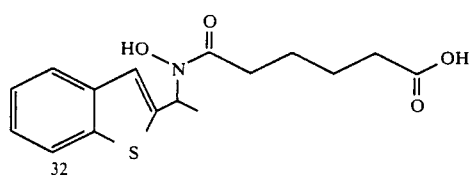

The desired product 32 was prepared by the method of Example 23 from 31. m.p. 157.9–158.9° C.; NMR (300 MHz, DMSO-d$_6$) 1.45–1.60 (7H, m), 2.2 (2H, bt), 2.4 (2H, bt), 5.9 (1H, bq), 7.28–7.38 (3H, m), 7.8 (1H, m), 7.9 (1H, m), 9.63 (1H, bs), 12.0 (1H, bs); MS: (M+H)+ =322.

Analysis Calc'd for C$_{16}$H$_{19}$NO$_4$S: C, 59.79; H, 5.96; N, 4.36.

Found: C, 59.77; H, 5 92; N, 4.31.

EXAMPLE 33

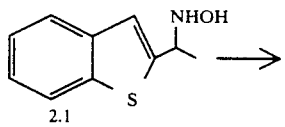

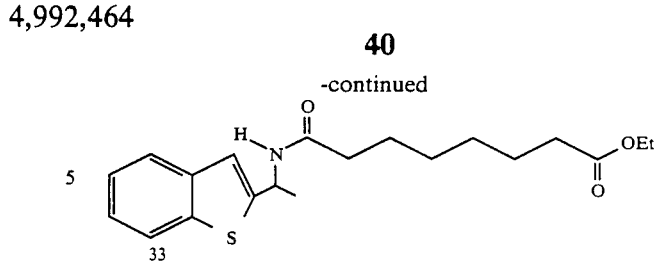

The desired product 33 was prepared by the method of Example 22 from 2.1 using monomethylester 1,8-octanedicarboxylic acid chloride instead of methyl glutaryl chloride. m.p. 49° C.; NMR (300 MHz, DMSO-d$_6$): 1.18 (3H, t), 1.25 (4H, m), 1.5 (4H, m), 1.58 (3H, d), 2.25 (2H, t), 2.38 (2H, m), 4.05 (2H, q), 5.9 (1H, bq), 7.28–7.38 (3H, m), 7.8 (1H, m), 7.9 (1H, m), 9.62 (1H, bs); MS: (M+H)+ =378.

Analysis Calc'd for C$_{20}$H$_{27}$NO$_4$S: C, 63.63; H, 7.21; N, 3.71.

Found: C, 63.49; H, 7.21; N, 3.65.

EXAMPLE 34

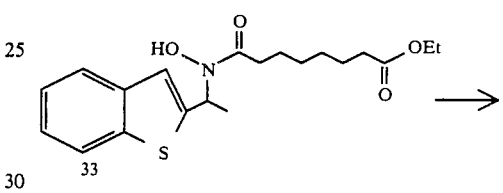

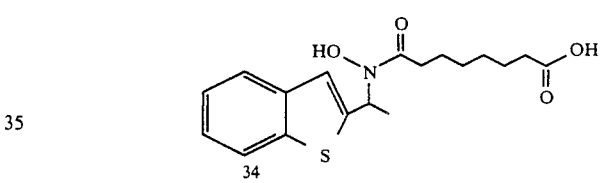

The desired product 34 was prepared by the method of Example 23 from 33. m.p. 140–141° C; NMR (300 MHz, DMSO-d$_6$): 1.28 (4H, m), 1.4–1.55 (4H, m), 1.58 (3H, d), 2.18 (2H, t), 2.38 (2H, bt), 5.9 (1H,bq), 7.28–7.38 (3H, m), 7.8 (1H, m), 7.9 (1H, m), 9.62 (1H, bs), 12.0 (1H, bs); MS: (M+H)+ =350.

Analysis Calc'd for C$_{18}$H$_{23}$NO$_4$S: C, 61.87; H, 6.63; N, 4.01.

Found: C, 61.55; H, 6.58; N, 3.96.

EXAMPLE 35

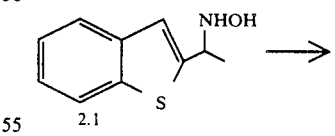

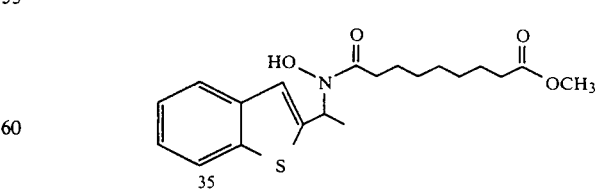

The desired product 35 was prepared by the method of Example 22 using monomethylester 1,9-nonanedicarboxylic acid chloride instead of methyl glutaryl chloride. m.p. 78.5–79.5° C.; NMR (300 MHz, DMSO-d$_6$): 1.23 (6H, m), 1.5 (4H, m), 1.58 (3H, d), 2.28 (2H, t), 2.38

(2H, d of t), 3.58 (3H, s), 5.9 (1H, bq), 7.28–7.38 (3H, m), 7.8 (1H, m), 7.9 (1H, m), 9.6 (1H, bs): MS: (M+H)+ =378.

Analysis Calc'd: C, 63.63; H, 7.21; N, 3.71.
Found: C, 63.66; H, 7.22; N, 3.70.

EXAMPLE 36

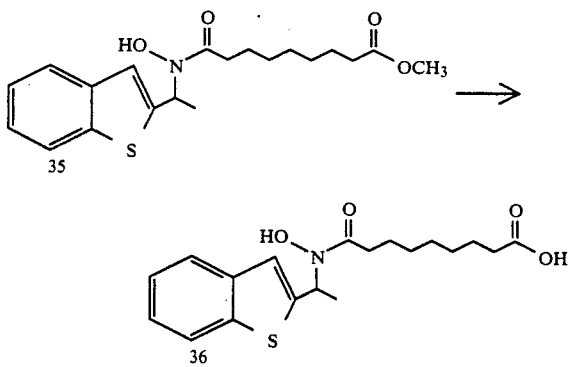

The desired product 36 was prepared by the method of Example 23 from 35. m.p. 136–137° C.; NMR (300 MHz DMSO-d6): 1.25 (6H, m), 1.4–1.55 (4H, m), 1.58 (3H, d), 2.18 (2H, t), 2.38 (2H, m), 5.9 (1H, bq), 7.25–7.38 (3H, m), 7.8 (1H, m), 7.9 (1H, m), 9.60 (1H, bs), 11.98 (1H, bs); MS: (M+H)+ =364.

Analysis Calc'd for $C_{19}H_{25}NO_4S$: C, 62.79; H, 6.93; N, 3.85.
Found: C, 62.43; H, 6.84; N, 3.8.

EXAMPLE 37

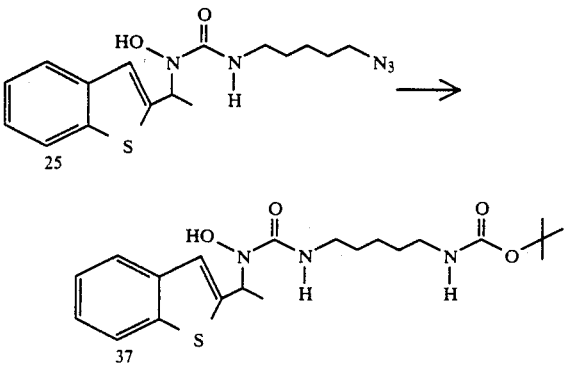

(a) The azide of Example 25 (7.50 g, 21.6 mmol) was dissolved in methanol (100 mL) and to this stirred solution was added triethylamine (3.50 g, 34.6 mmol) and 1,3-propanedithiol (3.52 g, 32.5 mmol) under nitrogen. After 3 days, the reaction was vacuum filtered and the white solid was washed with hexane and dried under vacuum to give 6.56 g of crude amine.

(b) To a stirred suspension of the crude amine (3.21 g, 10.0 mmol) in warm dry THF (180 mL) was added 3.40 g 15.5 mmol) of di-tert-butyl dicarbonate under nitrogen. After stirring overnight at ambient temperature, the suspension was vacuum filtered through celite, the solid washed thoroughly with THF and ethyl acetate, and the filtrate concentrated. Chromatography (silica gel, EtOAc-hexane, 30:70, 40:60, 50:50) gave pure product which crystallized from EtOAc-hexane. Vacuum filtration and drying yielded the desired BOC-amine 37 (1.69 g). m.p. 109–110° C.; NMR (300 MHz, DMSO-d6): 1.19 (m, 2), 1.35 (m, 4), 1.37 (s, 9), 1.51 (d, 3, J=7.0), 2.86 (q, 2, J=7.0), 3.02 (m, 2), 5.55 (q, 1, J=7.0), 6.75 (m, 1, NH), 7.00 (t, 1, J=5.9, NH), 7.25 (br s, 1), 7.30 (m, 2), 7.77 (m, 1), 7.88 m, 1), 9.18 (s, 1, OH); MS: (M+1)+ =422.

Analysis Calc'd for $C_{21}H_{31}N_3O_4S$: C, 59.83; H, 7.41; N, 9.97.
Found: C, 59.59; H, 7.48; N, 9.82.

EXAMPLE 38

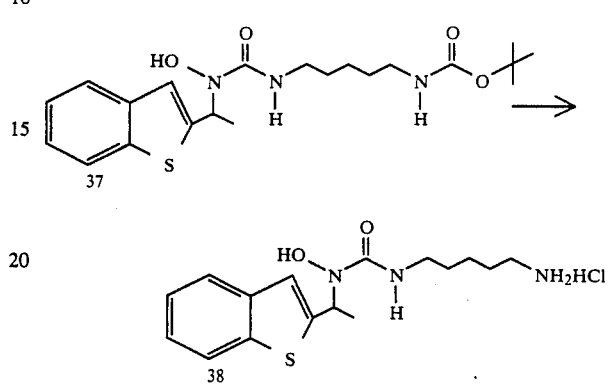

The BOC-protected compound produced in Example 37 (510 mg, 1.21 mmol) was dissolved in 4 N HCl dioxane solution (7.5 mL) and gas evolution was observed as the crystalline material dissolved. The clear solution was stirred for 5 minutes and then concentrated to a thick foamy syrup which crystallized on standing to yield 381 mg, 88% of 38. m.p. 142–144° C.; NMR (300 MHz, DMSO-d6): 1.26 (m, 2 , 1.41 (m, 2), 1.51(d, 3, J=7.0), 1.53 (m, 2), 2.71 (m, 2), 3.04 (m, 2), 5.54 (q, 1, J=7.0), 7.01 (t, 1, J=5.9, NH), 7.26 (br s, 1), 7.31 (m, 2), 7.77 (m, 1), 7.87 (m, 1), 7.89 (m, 3), 9.21 (s, 1, OH); MS: (M+1)+ =3.

Analysis Calc'd for $C_{16}H_{24}C_1N_3O_2S$: C, 53.70; H, 6.76; N, 11.74.
Found: C, 53.50; H, 6.81; N, II.54.

EXAMPLE 39

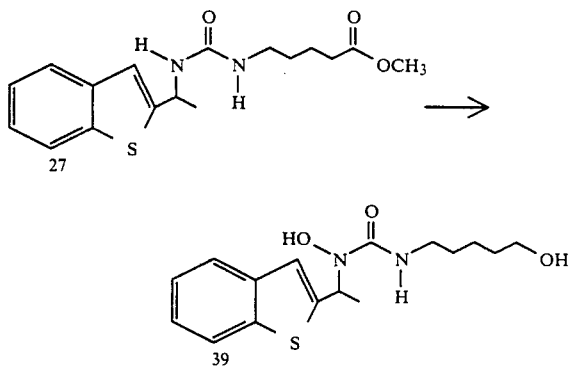

To a stirred solution of the ester prepared in Example 27 in dry THF (5 mL) was added 5 mL of 1 M lithium borohydride in THF under nitrogen. The reaction was stirred at ambient temperature overnight and then quenched by the addition of methanol (25 mL). After dilution with 10% aqueous citric acid (100 mL), the mixture was extracted with ethyl acetate (3×80 mL). The extracts were dried over MgSO4, filtered and concentrated. The crude product was chromatographed (silica gel, EtOAc-hexane, 50:50, 75:25, then EtOAc). Crystallization from EtOAc gave 417 mg of desired product 39. m.p. 130-131.5° C.; NMR (300 MHz, DMSO-d6): 1.24 (m, 2), 1.39 (m, 4), 1.51 (d, 3, J=7.0), 3.03 (m, 2), 3.35 (m, 2, obscured), 4.33 (t, 2, J=5.2, OH), 5.54 (q, 1 J=7.0), 6.99 (t, 1, J=5.9, NH), 7.25 (br s, 1), 7.31 (m, 2), 7.76 (m, 1), 7.87 m, 1), 9.17 (s, 1, OH); MS: (M+1)+ =3.

Analysis Calc'd for $C_{16}H_{22}N_2O_3S$: C, 59.60; H, 6.88; N, 8.69.

Found: C, 59.45; H, 6.90; N, 8.59.

EXAMPLE 40

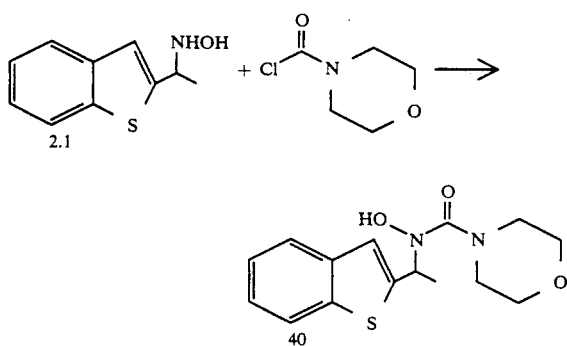

A solution of the hydroxylamine 2.1 (0.77 g, 5.29 mmol) and diisopropylethylamine (1.11 mL, 6.35 mmol) in dry dichloromethane (18 mL) was cooled to 0° C. and morpholinylcarbonylchloride was added in the same orpholinylcarbonylchloride was added in the same solvent (3 mL). The reaction was stirred overnight as it warmed to 25° C. and quenched by pouring into 10% aqueous HCl. The aqueous mixture was extracted with EtOAc. The organic layer was washed (2×saturated NaHCO3; 2×brine), dried with Na2SO4, filtered and concentrated in vacuo. The resulting residue was chromatographed (silica gel, EtOAc:hexanes, 20%) and afforded 0.65 g of 40. Recrystallization from ether/hexanes provided 40 as a waxy crystalline material. m.p. 129.5-130° C.; NMR (300 MHz, CDCl3) 1.73 (3H, d, J=7.0), 3.57 (4H, m), 3.72 (4H, t, J=4.5), 4.9(1H, q, J=7.0), 6.09 (1H, s), 7.2 (1H,s), 7.27-7.38 (2H, m), 7.7-7.8 (2H, m); MS: (M+H)+ =307.

Analysis Calc'd for $C_{15}H_{18}N_2O_3S$: C, 58.80; H, 5.92; N, 9.14.

Found: C, 58.69; H, 5.92; N, 9.08.

EXAMPLE 41

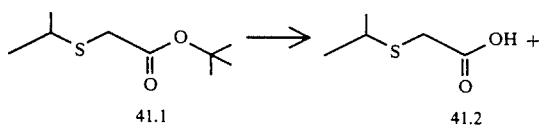

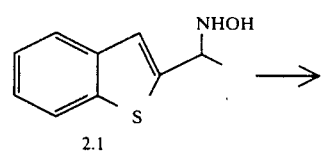

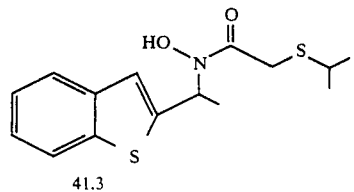

(a) To a stirred solution of t-butyl bromoacetate (24.83 mL, 153.8 mmol) and isopropyl thiol (15.70 mL, 169.2 mmol) in absolute methanol was added in a single portion triethylamine (25.72 mL, 184.6 mmol). The resulting solution was refluxed under N2 for 1 hour, cooled, filtered and concentrated in vacuo. The residue was taken up in ether and the organic layer washed (1×, Na2SO4, filtered and concentrated in vacuo . The resulting residue was vacuum distilled and t-butyl isopropylthioacetate (17.53 g, 60%) was collected in the fraction at 92° C. (14 mm Hg)[NMR (300 MHz, CDCl3) 1.28 (6H, d, J=7.0 Hz), 1.48 (9H, s), 3.07 (1H, septet, J=7.0 Hz), 3.17 (2H, s)]. The t-butyl ester was removed by stirring in a 1:1 (v:v) solution of trifluoroacetic acid and dichloromethane (375 mL) at 25° C. for 2 hours. The volatiles were removed in vacuo and three times the residue was taken up in toluene and concentrated in vacuo to provide the acid 41.2 (13.5 g), which was used without further purification. NMR (300 MHz, CDCl3) 1.70 (6H, d, J=6.0 Hz), 3.11 (1H, septet, J=6.0 Hz), 3.28 (2H, s), 11.29 (1H, br s).

(b) To a stirred solution of the product of step (a) (1.0 g, 7.5 mmol) in dry THF (15 mL) at −23° C. was added sequentially N-methyl morpholine (0.91 mL, 8.25 mmol) and pivaloyl chloride (0.92 mL, 7.5 mmol) and the resulting solution was stirred for 3 minutes. The hydroxylamine 2.(1.44 g, 7.5 mmol) was added in dry THF (15 mL), the cooling bath removed, and the reaction stirred until it had warmed to 25° C. The reaction was diluted with EtOAc and washed sequentially (2×, 10% HCl; 2×, saturated NaHCO3; 2×, brine) dried with Na2SO4, filtered and concentrated in vacuo. The resulting residue was chromatographed (silica gel, EtOAc:hexanes, 20%) and afforded 0.24 g of an off-white crystalline material which was recrystallized (cold ether:hexanes) to afford 0.15 g of 41.3 as white crystals. m.p. 83-84.5° C.; NMR (300 MHz, DMSO-d6) 1.18 (6H, d, J=7.0),1.58 (3H, d, J=7.0), 3.03 (1H, septet, J=7.0 Hz), 3.33 (2H, s), 5.87 (1H, br q, J=7.0 Hz), 7.27-7.4 (2H, m), 7.91 (2H, m), 9.82 (1H,s); MS: (M+H)+ =310.

Analysis Calc'd for $C_{15}H_{19}NO_2S_2(0.25\ H_2O)$ C, 57.39; H, 6.26; N, 4.46.

Found: C, 57.55; H, 6.09; N, 4.46.

EXAMPLE 42

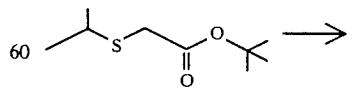

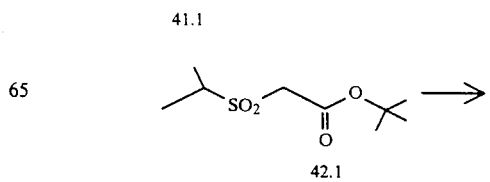

-continued

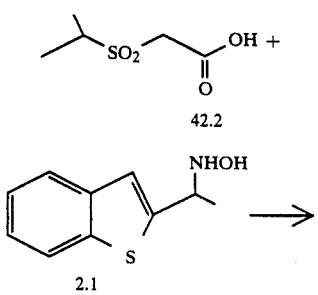

42.2

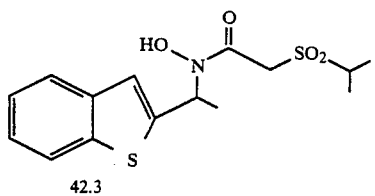

42.3

To a stirred solution of compound 41.1 (5.00 g, 26.3 mmol) at −23° C. in dichloromethane (105 mL) was added m-chloroperoxy-benzoic acid (12.48 g, 72.3 mmol) in small portions. After complete addition the reaction was stirred for 15 minutes, diluted with EtOAc and washed sequentially (2×, saturated aqueous NaHSO3; 2×, saturated Na2CO3; 2×, brine), dried with Na2SO4, filtered and concentrated in vacuo. The resulting residue was chromatographed (silica gel, 20% EtOAc:hexanes) to afford 4.11 g of the intermediate 42.1 [NMR (300 MHz, CDCl3) 1.42 (6H, d, J=7.0Hz), 1.52 (9H, s), 3.56(1H, septet, J=7.0 Hz), 3.89 (2H, s)]. The t-butyl group was removed following the procedure in Example 41 to afford 4.81 g of acid 42.2 which was utilized without further characterization.

To a stirred solution of compound 42.2 (1.66 g, 9.97 mmol) at −23° C. in dry THF was added sequentially N-methyl morpholine (1.11 g, 11.0 mmol) and isobutyl chloroformate (1.43 g, 10.5 mmol). After stirring for 5 minutes at −23° C., the hydroxylamine 2.1 (1.93 g, 9.97 mmol) was added in a single portion, the cooling bath was removed, and the resulting solution stirred for 1 hour as it warmed to 25° C. The reaction was then diluted with EtOAc and processed as described in Example 41. The resulting residue was chromatographed (silica gel, EtOAc:hexanes, 20%) and afforded 0.5 g of product. Recrystallization from ether/hexanes provided 42.3 as a crystalline material. m.p. 163-164° C.; NMR (300 MHz, DMSO-d6) 1.27 (6H, d, J=7.0 Hz), 1.61 (3H, d, J=7.0Hz), 3.62 (1H, septet, J=7.0 Hz), 4.39 (2H, s), 5.93 (1H, q, J=7.0 Hz), 7.2-7.42 (3H, m), 7.8 (1H, m), 7.93 (1H, m), 10.27 (1H, s); MS: (M+H)+ =342.

Analysis Calc'd for C15H19NO4S2: C, 52.76; H, 4.10; N, 5.61.
Found: C, 52.43; H, 4.05; N, 5.52.

EXAMPLE 43

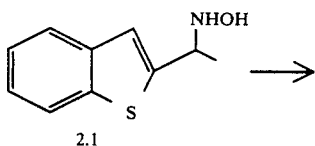

2.1

-continued

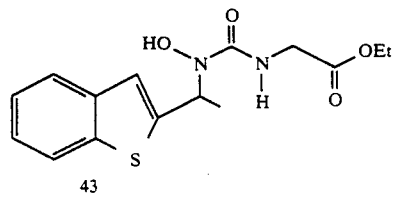

43

To a magnetically stirred solution of 2.1 (2.0 g, 10.4 mmol) in dry THF (50 mL) was added dropwise ethyl isocyanatoacetate (1.40 mL, 12.4 mmol) under dry nitrogen. After 1 hour, the reaction was concentrated and the residue was recrystallized from ethyl acetate-hexane; vacuum filtration and drying gave 2.6 g (77%) of 43. m.p. 127-129° C.; NMR (300 MHz, DMSO-d6): 1.17 (t, 3, J=7.5), 1.53 (d, 3, J=7.5), 3.78 (m, 2), 4.07 (q, 2, J=7.5), 5.55 (q, 1, J=7.5), 7.34 (m, 4), 7.83 (m, 2), 9.42 (s, 1); MS: (M+1)+ =3.

EXAMPLE 44

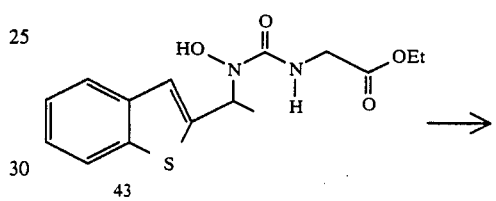

43

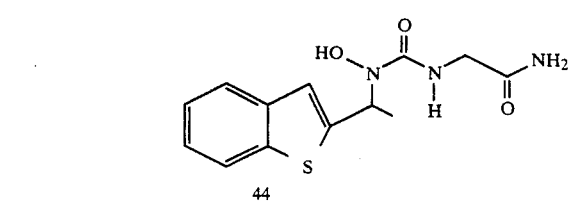

44

To a stirred suspension of NH4Cl (171 mg, 6.4 mmol) in dry CH2Cl2 at −78° C, was added Me3Al (3.2 mmol). The reaction stirred at −78° C. for 15 minutes before being warmed to −20° C. for 30 minutes. The reaction was warmed to room temperature and then the ester 43 (500 mg, 1.6mmol) was slowly added as a solution in CH2Cl2 (5 mL). The reaction was heated at reflux for three days. Aqueous HCl (2 mL, 1.6M) was added slowly. A solid precipitated which was collected by vacuum filtration, then suspended in 10% HCl (10 mL) and stirred for three days. The solid was collected and dried (vacuum oven, 100° C., 1 day) to give amide 44 (43% yield). m.p. 165° C. dec; NMR (300 MHz, DMSO-d6) 1.52 (3H, D, J=7.5Hz); 3.64 (2H, m); 5.55 (1H, q, J=7.5Hz); 7.03 (2H, m); 7.30 (4H, m); 7.83 (2H, m); 9.36 (1H, s); MS (M+H)+ =294.

EXAMPLE 45

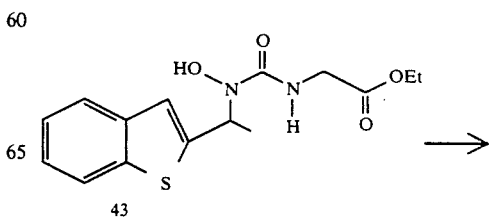

43

47

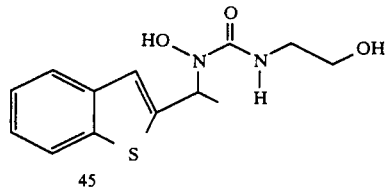

To a magnetically stirred solution of 43 (5.20 g, 16.13 mmol) in 40 mL of dry THF was added dropwise at room temperature 18.0 mL (36.0 mmol) of 2M lithium borohydride in THF under dry nitrogen. The turbid reaction was stirred at ambient temperature overnight, then quenched by the dropwise addition of methanol (35 mL). After 4 hours, the reaction was concentrated, the residue was treated with 125 mL of 10% aqueous citric acid and extracted with ethyl acetate (3×100 mL) . The extracts were dried (MgSO$_4$), filtered and concentrated to a clear yellow oil, which crystallized upon standing overnight. The product was recrystallized from EtOAc-hexane, vacuum filtered and dried to furnish 3.61g (12.88 mmol, 80%) of 45. m.p. 133-135° C.; NMR (300 MHz, DMSO-d$_6$): 1.51 (d, 3, J=7.0), 3.13 (m, 2), 3.39 (q, 2, J=6.8), 4.65 (t, 1, J=5.5, OH), 5.56 (q, 1, J=7.0), 6.90 (t, 1, J=5.7, NH), 7.26 (br s, 1), 7.31 (m, 2), 7.76 (m, 1), 7.88 (m, 1), 9.24 (s, 1, OH); MS: (M+1)$^+$=281.

Analysis Calc'd for C$_{13}$H$_{16}$N$_2$O$_3$S: C, 55.70; H, 5.75; N, 9.99.

Found: C, 55.65; H, 5.75; N, 9.81

EXAMPLE 46

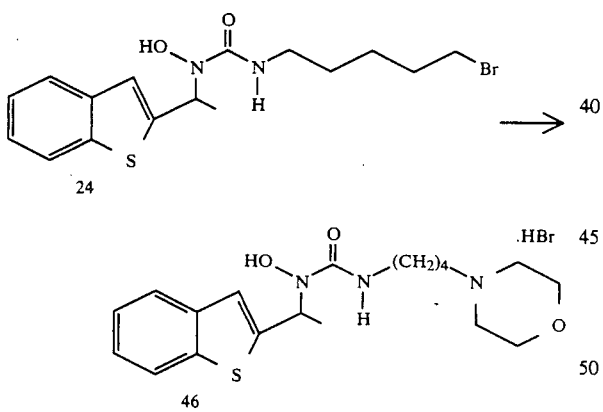

To a magnetically stirred solution of 24 (2.08 g, 5.40 mmol) was added dropwise 0.50 mL (0.50 g, 5.74 mmol) of morpholine under nitrogen. The reaction was stirred at ambient temperature overnight, then the crystalline product was vacuum filtered, washed with ethyl acetate-hexane and dried to afford 1.48 g (3.13 mmol, 58%) of 46. m.p. 125-127° C.; NMR (300 MHz, DMSO-d$_6$) : 1.20 (m, 2), 1.39 (m, 4), 1.51 (d, 3, J=7.0), 2.24 (t, 2, J=7.4), 3.03 (q, 2, J=6.6), 3.08 (m, 4), 3.56 (t, 2, J=4.6), 3.75 (m, 4), 5.53 (q, 1, J=7.0), 7.02 (t, 1, J=5.9, NH), 7.25 (s,1), 7.31 (m, 2), 7.76 (m, 1), 7.87 (m, 1), 9.18 (s, 1, OH); MS: (M+1)$^+$=392.

Analysis Calc'd for C$_{20}$H$_{29}$N$_3$O$_3$S HBr: C, 50.84; H, 6.40; N, 8.89.

Found: C, 50.58; H, 6.; N, 8.71.

EXAMPLE 47

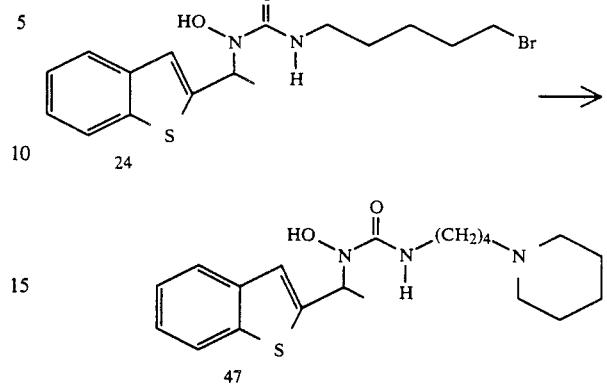

To a magnetically stirred solution of 24 (2.50 g, 6.49 mmol) in dry THF (3.0 mL) was added dropwise 5.0 mL of piperidine to give a turbid yellow solution. After stirring overnight, the reaction was diluted with ethyl acetate (100 mL) and was shaken with 35 L of 0.5 N NaOH. The aqueous layer was extracted with ethyl acetate (2×60 mL) and the combined organic layer was dried, filtered, and concentrated to provide 2.09 g (5.37 mmol, 83%) of crystalline 47. m.p. 129-130° C.; NMR (300 MHz, DMSO-d$_6$) 1.19 (m, 2), 1.3-1.5 (m, 10), 1.52 (d, 3, J=7.0), 2.16 (t, 2, J=7.0), 2.28 (m, 4), 3.03 (q, 1, J=7.0), 3.36 (m, 2), 5.53 (q, 1, J=7.0), 6.99 (t, 1, J=6.8, NH), 7.25 (s, 1), 7.31 (m, 2), 7.76 (m, 1), 7.87 (m, 1), 9.18 (s, 1, OH); MS: (M+1)$^+$=390.

Analysis Calc'd for C$_{21}$H$_{31}$N$_3$O$_2$S: C, 64.75; H, 8.02; N, 10.79.

Found: C, 64.68; H, 7.90; N, 10.70.

EXAMPLE 48

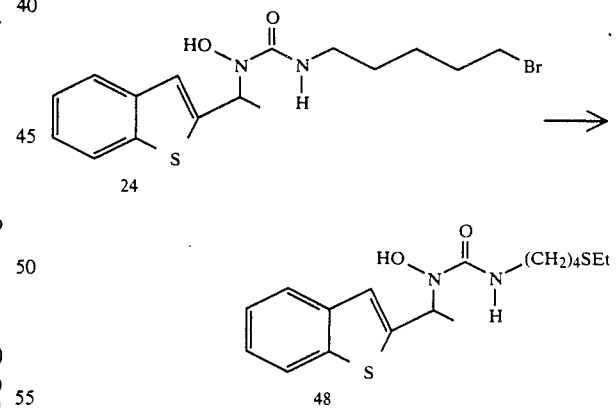

To a magnetically stirred suspension of sodium hydride (350 mg, 14.6 mmol) in dry THF (20 mL) was added dropwise ethanethiol (1.87 g, 30.0 mmol) under dry nitrogen. The resulting thick white suspension was stirred 15 minutes, then a solution of (3.85 g, 10.0 mmol) in 5.0 mL of dry THF was added dropwise. After stirring overnight, the reaction was added to saturated aqueous NH$_4$Cl (200 mL) and extracted with ethyl acetate (3×100 mL). The extracts were dried (MgSO$_4$), filtered and concentrated. Chromatography on a 100 g column of silica gel using EtOAc-hexane (20:80, 30:70, 40:60, 50:50) afforded 2.75 g (7.50 mmol, 75%) of white crystalline 48. m.p. 75–76° C.; NMR (300 MHz, DMSO-d$_6$) 1.16 (t, 3, J=7.4), 1.27 (m, 2), 1.35–1.50 (m, 4), 1.51 (d, 3, J=7.0), 2.41 (t, 2, J=7.4), 2.46 (q, 2, J=7.4), 3.04 (q, 2, J=6.4), 5.54 (q, 1, J=7.0), 7.00 (t, 1, J=5.9, NH), 7.25 (s, 1), 7.30 (m, 2), 7.76 (m, 1), 7.87 (m, 1), 9.17 (s, 1, OH).

Analysis Calc'd for C$_{18}$H$_{26}$N$_2$O$_2$S$_2$: C, 58.98; H, 7.15; N, 7.64.
Found: C, 58.80; H, 7.02; N, 7.54.

EXAMPLE 49

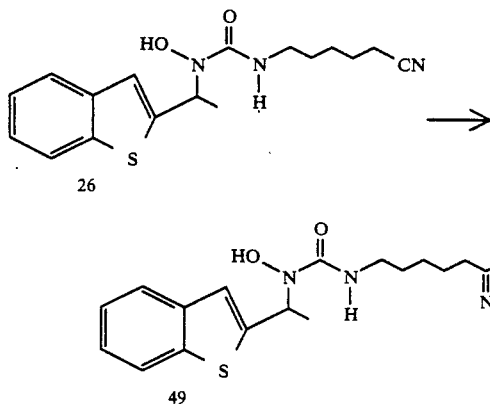

To a solution of the nitrile 26 (0.43 g, 1.3 mmol) in ethanol (30 mL) was added a solution of hydroxylamine hydrochloride (0.18 g, 2.7 mmol) in water (10 mL) adjusted to pH of 8. The reaction was warmed at 50° C. for 44 hours and the mixture was concentrated to about half the original volume and extracted with ether. The extracts were dried (MgSO$_4$), filtered, and concentrated. Dichloromethane was added to the residue and the product 49 was collected by filtration as a white powder. m.p. 134–136° C.(dec.); NMR (300 MHz, DMSO-D$_6$) 1.15–1.32 (2H, m), 1.35–1.55 (7H, m), 2.14 (2H, t, J =7.5 Hz),3.03 (2H, m), 5.55 (1H, m), 7.85–7.91 (2H, m), 8.22 (1H, s), 9.19, (1H, s), 9.31 (1H, s): MS M+H+ =381.

EXAMPLE 50

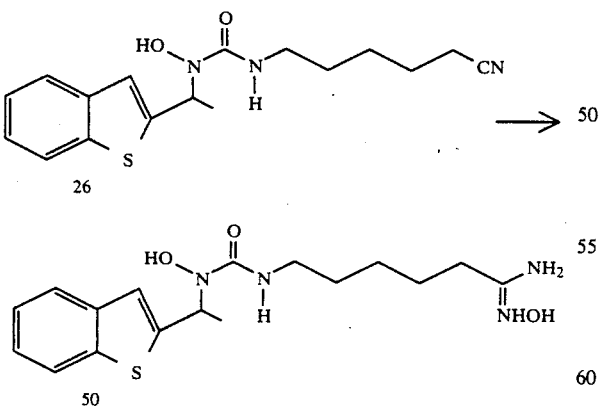

The desired product 50 was prepared according to the procedure of example 49 except only one equivalent of hydroxylamine hydrochloride was used. NMR (300MHZ, DMSO-D$_6$) 1.12–1.3 (2H, m), 1.32–1.55 (7H, m,), 1.91 (2H, t, J=7.5 Hz), 3.02 (2H, m), 5.30 (2H, s), 5.55 (1H, q, J=7.0 Hz), 7.02 (1H, m), 7.25–7.37 (3H, m), 7.75–7.79 (1H, m), 7.85–7.91 (1H, m), 8.68 (1H, s), 9.19, (1H, s); MS M+H+ =365.

EXAMPLE 51

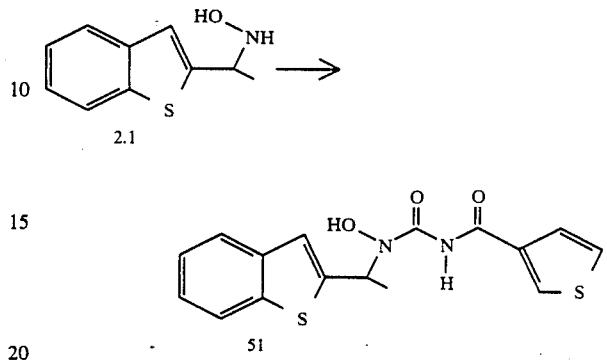

According to the method of Example 1 the desired compound 51 is prepared by reaction of 2.1 with thien-3-ylacetyl-isocyanate.

EXAMPLE 52

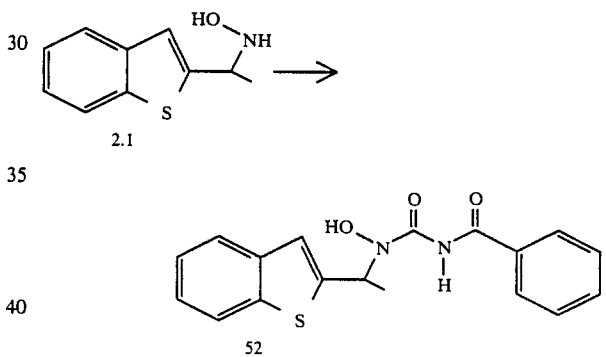

According to the method of Example 1 the desired compound 52 is prepared by reaction of 2.1 with benzoylisocyanate.

EXAMPLE 53

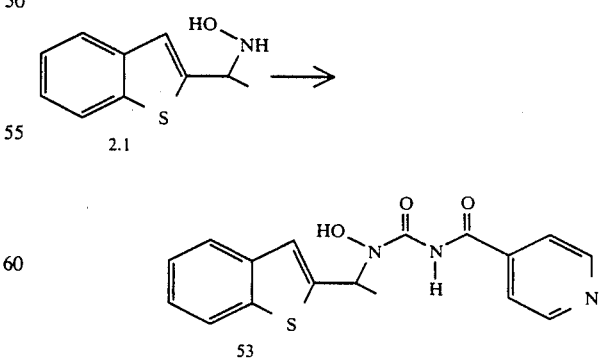

According to the method of Example 1 the desired compound 53 is prepared by reaction of 2.1 with 4-pyridylacylisocyanate.

EXAMPLE 54

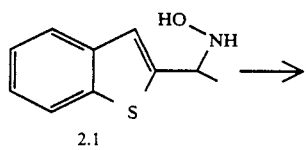
2.1

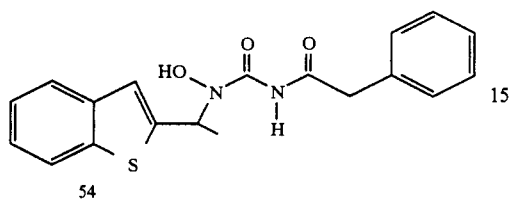
54

According to the method of Example 1 the desired compound 54 is prepared by reaction of 2.1 with benzylacetylisocyanate.

EXAMPLE 55

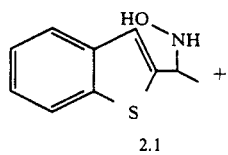
2.1

+

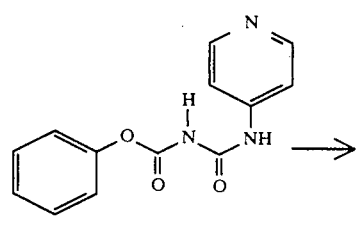
55.1

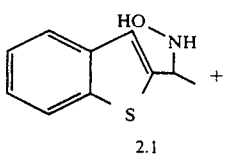
55.2

According to the method of Example 2 the desired compound 55.2 is prepared by reaction of 2.1 with 55.1.

EXAMPLE 56

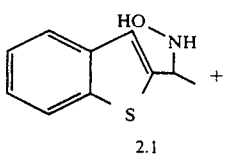
2.1

-continued

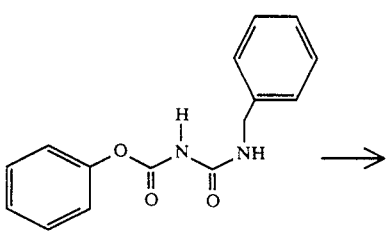
56.1

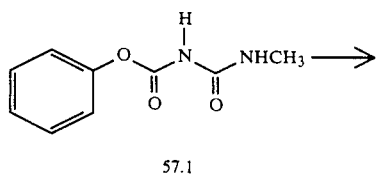
56.2

According to the method of Example 2 the desired compound 56.1 is prepared by reaction of 2.1 with 56.1.

EXAMPLE 57

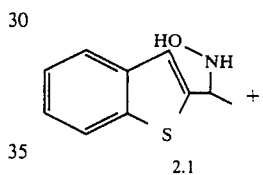
2.1

+

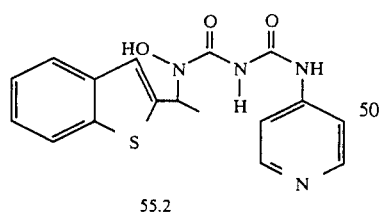
57.1

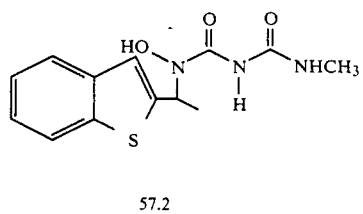
57.2

According to the method of Example 2 the desired compound 57.2 is prepared by reaction of 2.1 with 57.1.

EXAMPLE 58

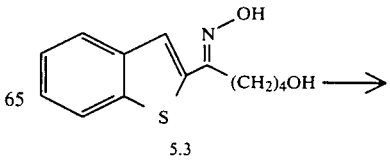
5.3

-continued

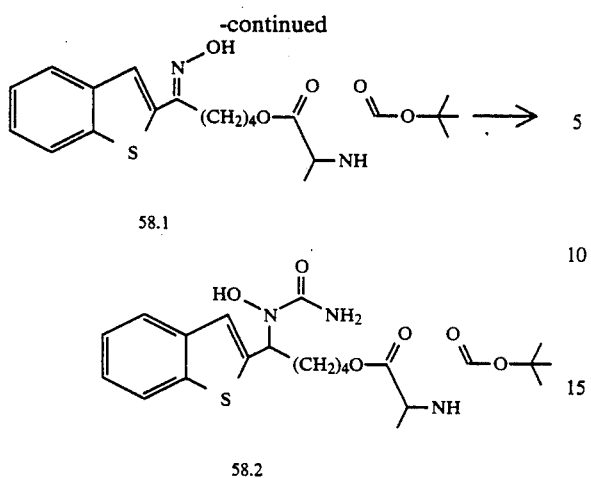

58.1

58.2

Esterification of 5.3 with the aminoacid derivative N-BOC-alanine provides the intermediate 58.1 which is converted to the desired compound 58.2 according to the methods used for Example 3.

EXAMPLE 59

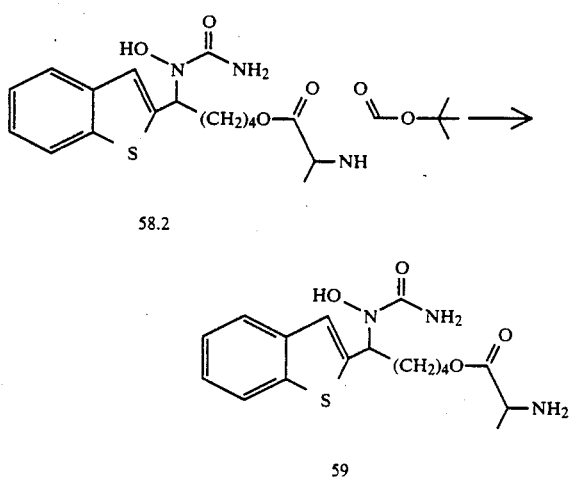

58.2

59

Removal of the BOC-group by standard procedures in 58.2 provides the desired compound 59.

EXAMPLE 60

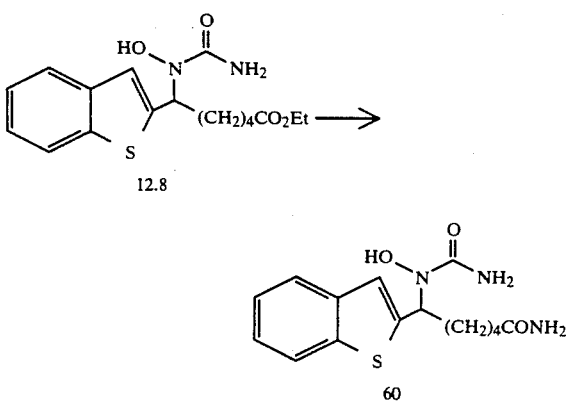

12.8

60

The desired amide 60 is prepared from the ester 12.8 by standard procedures.

EXAMPLE 61

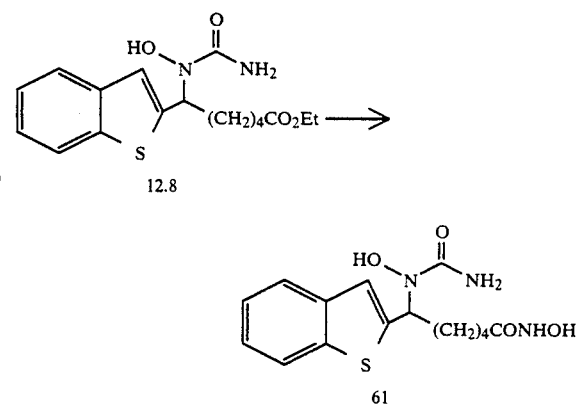

12.8

61

The desired hydroxamate 61 is prepared from the ester 12.8 by treatment with hydroxylamine.

EXAMPLE 62

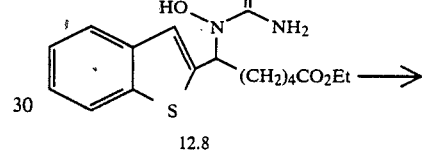

12.8

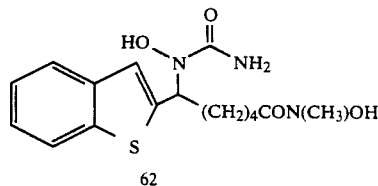

62

The desired hydroxamate 62 is prepared from the ester 12.8 by treatment with methylhjydroxylamine.

EXAMPLE 63

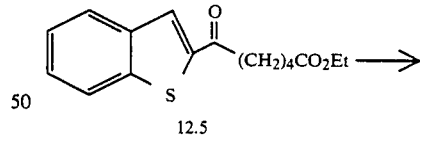

12.5

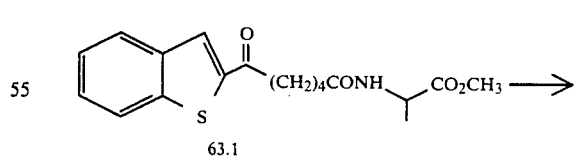

63.1

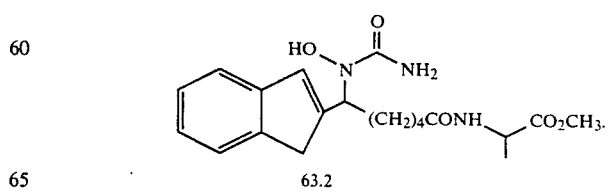

63.2

The intermediate 63.1 is prepared from 12.5 by treatment with alanine methylester and is subsequently processed according to the method of Example 12 to provide the desired product 63.2.

EXAMPLE 64

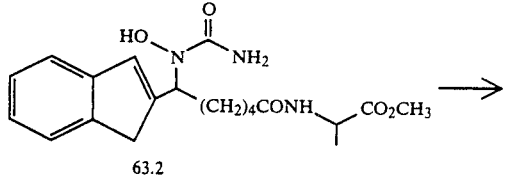

63.2

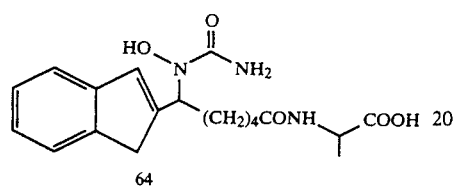

64

Compound 63.2 is saponified to provide 64.

EXAMPLE 65

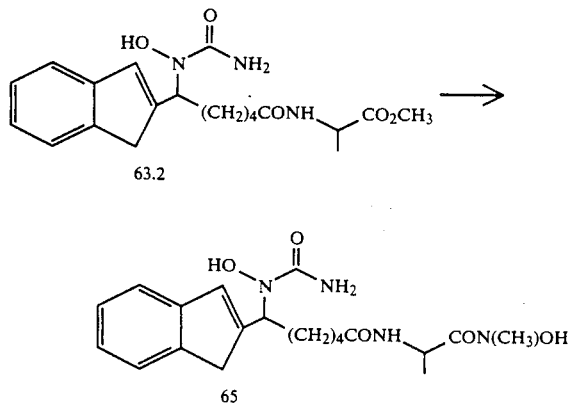

The desired hydroxamate 65 is prepared from the ester 63.2 by treatment with methylhydroxylamine.

EXAMPLE 66

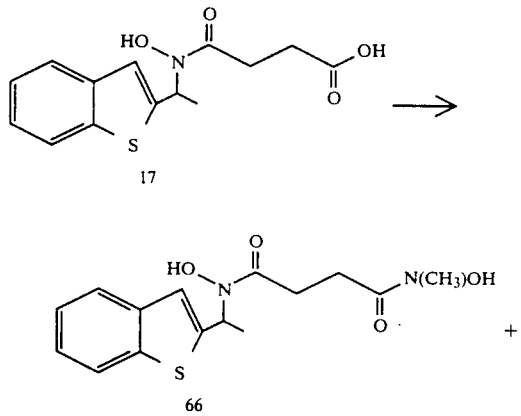

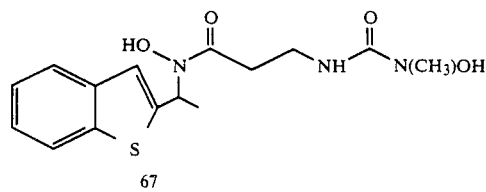

67

The desired compounds 66 and 67 are prepared from 17 according to the procedure of Example 18 and the products are separated by chromatography.

EXAMPLE 68

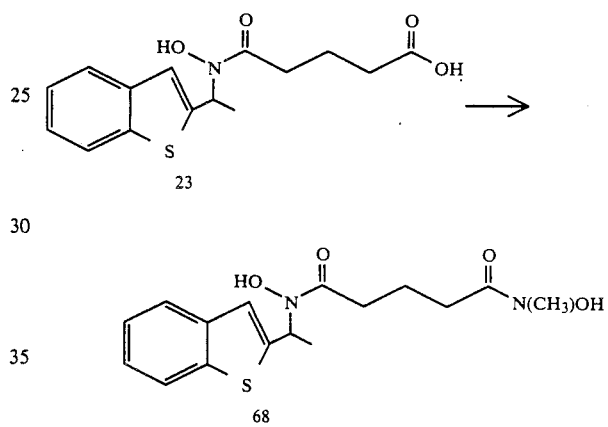

The desired product 68 is prepared from 23 by treatment with methylhydroxylamine.

EXAMPLE 69

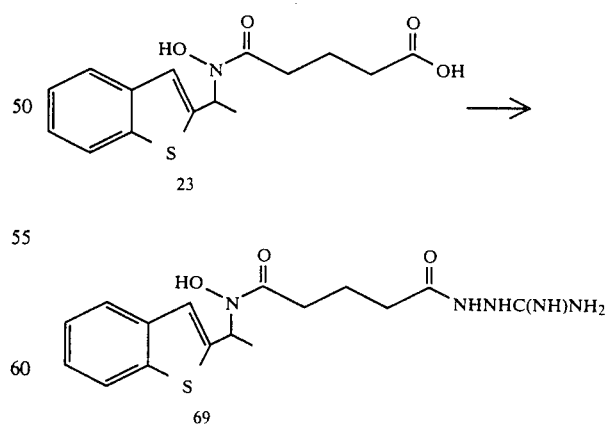

The desired product 69 is prepared from 23 by treatment with aminoguanidine bicarbonate.

EXAMPLE 70

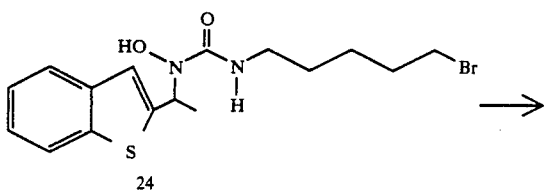
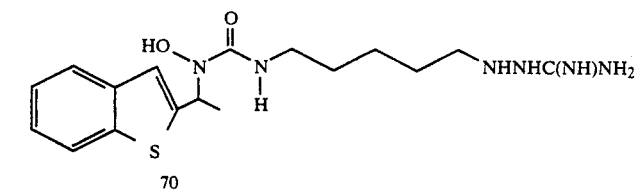
The desired product 70 is prepared from 24 by treatment with aminoguanidine bicarbonate.
EXAMPLE 71
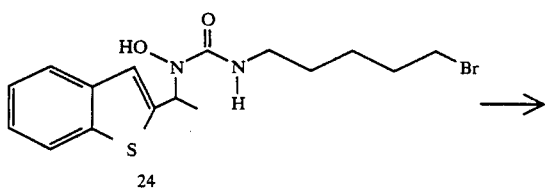
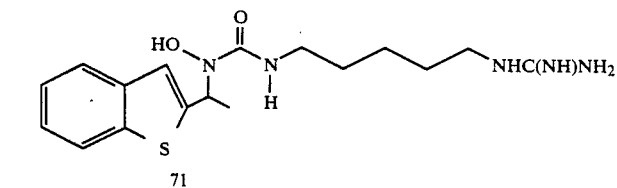
The desired product 17 is prepared from 24 by treatment with guanidine.
EXAMPLE 72
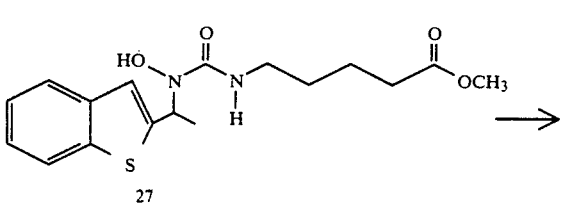
The desired product 72 is prepared from 27 by treatment with methylhydroxylamine.
EXAMPLE 73
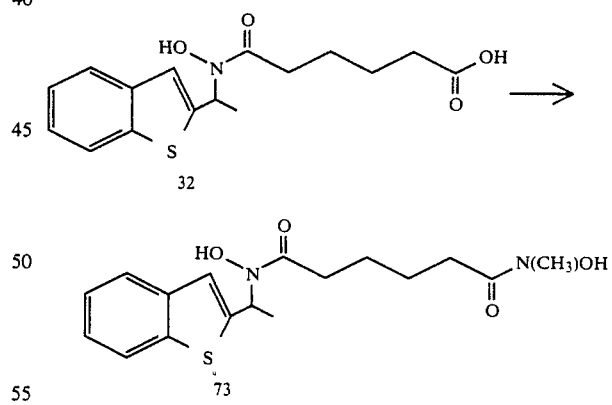
The desired product 73 is prepared from 32 by treatment with methylhydroxylamine.
EXAMPLE 74
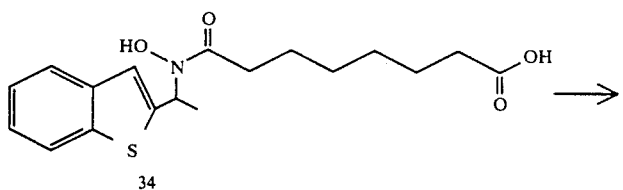

-continued

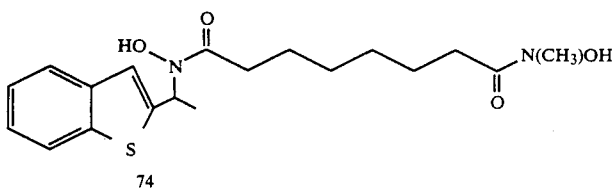
74

The desired product 74 is prepared from 34 by treatment with methylhydroxylamine.

EXAMPLE 75

The desired product 75 is prepared from 38 by treatment with trimethylsilylisocyanate followed by aqueous hydrolysis.

EXAMPLE 76

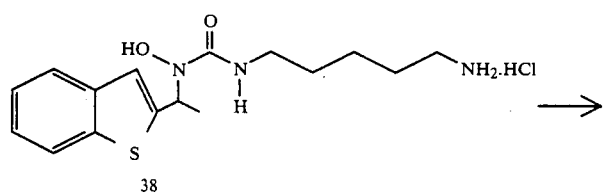
38

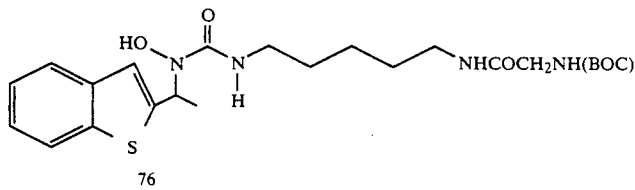
76

The desired product 76 is prepared from 38 by treatment with ClCOCH$_2$NH(BOC) in the presence of triethylamine.

EXAMPLE 77

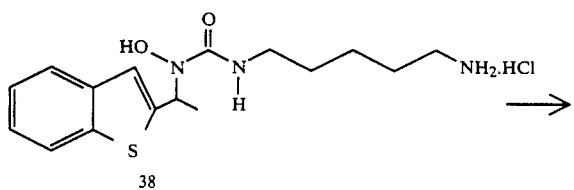
38

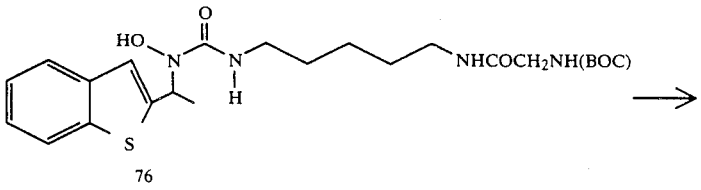
76

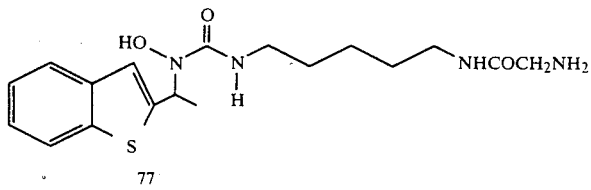
77

The desired product 77 is prepared from 76 by a standard method for removing the BOC group.

EXAMPLE 78

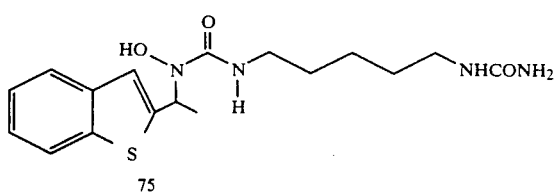
75

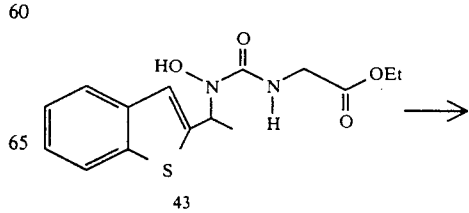
43

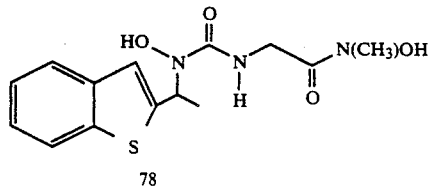

78

The desired product 78 is prepared from 43 by treatment with methylhydroxylamine.

EXAMPLE 79

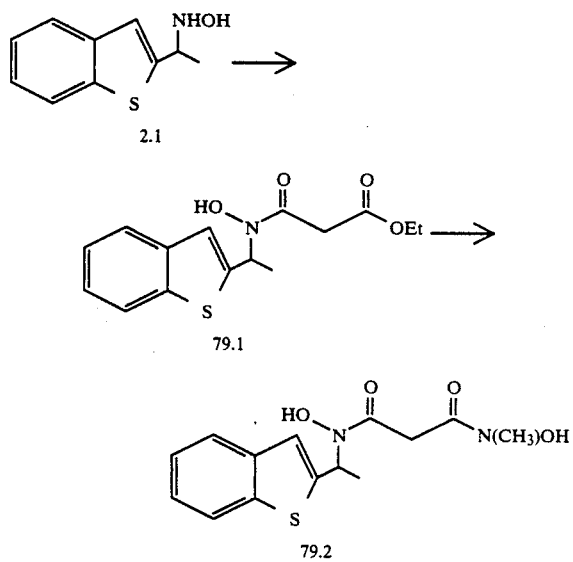

Reaction of intermediate 2.1 with ethyl malonate monoacid chloride provides 79.1 which is converted to the desired product 79.2 by treatment with methylhydroxylamine.

Inhibition of 5-Lipoxygenase

Inhibition of 5-lipoxygenase activity was determined using the 20,000× g supernatant from homogenized RBL-1 cells in a similar manner as that described by Dyer and coworkers (Dyer, R. D.; Haviv, F.; Hanel, A. M.; Bornemier, D. A.; Carter, G. W., Fed. Proc., Fed. Am. Soc. Exp. Biol. 1984, 43, 1462A). Inhibitory potencies for representative examples of this invention are listed in Table 1. $IC_{50}$ values (concentration of compound producing 50% enzyme inhibition) were calculated by linear regression analysis of percentage inhibition versus log inhibitor concentration plots.

TABLE 1

In vitro 5-lipoxygenase inhibitory potency of selected compounds of this invention.

| Example | $IC_{50}$ (μM) |
| --- | --- |
| 1 | 1.5 |
| 2 | 1.0 |
| 3 | 3.8 |
| 4 | 2.4 |
| 5 | 1.5 |
| 6 | 0.17 |
| 7 | 0.19 |
| 8 | 1.1 |
| 9 | 1.1 |
| 10 | 0.53 |
| 11 | 0.8 |
| 12 | 0.21 |
| 13 | 7.1 |
| 14 | 1.3 |
| 15 | 0.5 |
| 16 | 0.5 |
| 17 | 33 |
| 18 | 2.8 |
| 19 | 3.3 |
| 20 | 3.5 |
| 21 | 1.1 |
| 22 | 0.3 |
| 23 | 27 |
| 24 | 0.09 |
| 25 | 0.10 |
| 26 | 0.27 |
| 27 | 0.21 |
| 28 | 2.2 |
| 29 | 2.1 |
| 30 | 32 |
| 31 | 0.17 |
| 32 | 6.4 |
| 33 | 0.59 |
| 34 | 2.0 |
| 35 | 0.21 |
| 36 | 0.7 |
| 37 | 0.68 |
| 38 | 0.18 |
| 39 | 0.42 |
| 40 | 0.9 |
| 41 | 0.29 |
| 42 | 3.9 |
| 43 | 0.72 |
| 44 | 1.6 |
| 45 | 1.8 |
| 46 | 1.1 |
| 47 | 0.84 |
| 48 | 0.11 |
| 49 | 0.38 |
| 50 | 0.43 |

Inhibition of the biosynthesis of leukotrienes in vivo after oral administration of compound was determined using a rat peritoneal anaphylasix model in a similar manner as that described by Young and coworkers (Young, P. R.; Dyer, R. D.; Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compounds were administered by gavage one hour prior to the antigen challenge. Inhibitory potencies for representative examples of this invention are listed in Table 2. Percent inhibition values were determined by comparing the treatment group to the mean of the control group. From the results of this assay it is demonstrated that compounds of this invention are orally effective in preventing the in vivo biosynthesis of leukotrienes.

TABLE 2

In Vivo inhibition of leukotriene biosynthesis by oral administration.

| Example | % Inhibition at 200 μmol/kg oral dose |
| --- | --- |
| 3 | 44% |
| 11 | 39% |
| 17 | 36% |
| 26 | 49% |
| 45 | 70% |

What is claimed is:

1. A compound having the formula

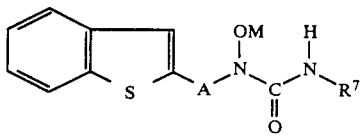

wherein

A is alkylene of from one to twelve carbon atoms or alkenylene of from two to fourteen carbon atoms;

M is selected from the group consisting of
hydrogen,
a pharmaceutically acceptable cation, and
a metabolically cleavable group;

$R^7$ is selected from the group consisting of
hydroxyl substituted alkyl of from one to twelve carbon atoms,
carboxyl substituted alkyl of from one to twelve carbon atoms and the pharmaceutically acceptable acid addition salts thereof, and
ethoxycarbonyl substituted alkyl of from one to twelve carbon atoms.

2. A pharmaceutical composition for inhibiting lipoxygenase activity in a mammal in need of such treatment comprising a pharmaceutical carrier and a therapeutically effective amount of a compound of claim 1.

3. A method for inhibiting lipoxygenase activity in a mammal in need of such treatment comprising administering to the mammal a therapeutically effective amount of a compound of claim 1.

* * * * *

UNITED STATES PATENT AND TRADEMARK OFFICE
CERTIFICATE OF CORRECTION

PATENT NO. : 4,992,464            Page 1 of 3

DATED : February 12, 1991

INVENTOR(S) : DEE W. BROOKS; JAMES B. SUMMERS; ROBERT G. MAKI; JOSEPH F. DELLARIA; JIMMIE L. MOORE;

It is certified that error appears in the above-identified patent and that said Letters Patent is hereby corrected as shown below:

Title Page, Column 2, Line 9: Replace "--O(CH)$_2$"
          with -- --O(CH$_2$)$_p$--.

Title Page, Column 2, Line 9: After "--O(CH$_2$)" insert -- -- CON(R)$_2$--.

Title Page, Column 2, Line 10: Replace "--O(CH)$_p$O(CH$_2$)-" with -- --O(CH$_2$)$_p$O(CH$_2$)- --.

Title Page, Column 2, Line 32: After "R5" insert --are--.

Title Page, Column 2, Line 39: After "of" delete --a--.

Column 12, line 15: Replace "(2H, sm)" with --(2H, m)--.

Column 19, line 58: Replace "C$_2$CL$_2$" with --CH$_2$Cl$_2$--.

Column 20, line 13: Replace "(2H,," with --(2H,m)--.

Column 24, line 23: Replace "51 04;" with --51.04--.

Column 24, line 24: After "N," insert --9.92.--.

Column 25, line 51: Replace "(2H, &," with --(2H, t,--.

Column 27, line 9: Replace "7.3I" with --7.31--.

Column 27, line 10: Replace "M+323." with --M+=323.--.

Column 28, line 45: After "(3H, m)" insert --,--.

UNITED STATES PATENT AND TRADEMARK OFFICE
CERTIFICATE OF CORRECTION

Page 2 of 3

PATENT NO. : 4,992,464
DATED : February 12, 1991
INVENTOR(S) : DEE W. BROOKS; JAMES B. SUMMERS; ROBERT G. MAKI; JOSEPH F. DELLARIA; JIMMIE L. MOORE It is certified that error appears in the above-identified patent and that said Letters Patent is hereby corrected as shown below:

Column 28, line 46:  Replace "$C_{18}H_{23}N_eO_3S:$" with
--$C_{18}H_{23}N_3O_3S:$--.

Column 30, line 28:  Replace "59 41;" with --59.41--.

Column 30, line 66:  Replace "$C_{14}H_{15}NOhd\ _4S$--.
--$C_{14}H_{15}NO_4S$--.

Column 32, line 31:  Replace "$C_{16}H_{2\text{-}}N_2O_4S$" with
--$C_{16}H_{20}N_2O_4S$--.

Column 32, line 33:  Replace "8 18" with --8.18--.

Column 33, line 42:  Replace "(2H, ," with --(2H, m),--.

Column 33, line 46:  Replace "6.11." with --6.11;--.

Column 34, line 65:  Replace "12 mL)" with --(12 mL)--.

Column 35, line 7:   Replace "7 8" with --7.8--.

Column 37, line 65:  Replace "2I(b)" with --21(b)--.

Column 41, line 25:  Replace "MHz DMSO-$d_6$):" with
--"MHz, DMSO-$d_6$):--

UNITED STATES PATENT AND TRADEMARK OFFICE
CERTIFICATE OF CORRECTION

PATENT NO. : 4,992,464                                            Page 3 of 3

DATED : February 12, 1991

INVENTOR(S) : DEE W. BROOKS: JAMES B. SUMMERS: ROBERT G. MAKI: JOSEPH F. DELLARIA: JIMMIE L. MOORE

It is certified that error appears in the above-identified patent and that said Letters Patent is hereby corrected as shown below:

Column 42, line 41: Replace "I1.54" with --11.54--.

Signed and Sealed this

Seventeenth Day of November, 1992

Attest:

DOUGLAS B. COMER

Attesting Officer      Acting Commissioner of Patents and Trademarks